US010918529B2

(12) United States Patent
Venturino et al.

(10) Patent No.: US 10,918,529 B2
(45) Date of Patent: Feb. 16, 2021

(54) ABSORBENT CORES AND METHODS FOR FORMING ABSORBENT CORES

(71) Applicant: Kimberly-Clark Worldwide, Inc., Neenah, WI (US)

(72) Inventors: Michael B. Venturino, Appleton, WI (US); Joseph J. Sina, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 145 days.

(21) Appl. No.: 16/086,459

(22) PCT Filed: Mar. 31, 2016

(86) PCT No.: PCT/US2016/025181
§ 371 (c)(1),
(2) Date: Sep. 19, 2018

(87) PCT Pub. No.: WO2017/171781
PCT Pub. Date: Oct. 5, 2017

(65) Prior Publication Data
US 2019/0083324 A1    Mar. 21, 2019

(51) Int. Cl.
*A61F 13/539* (2006.01)
*A61F 13/15* (2006.01)
(Continued)

(52) U.S. Cl.
CPC .. *A61F 13/15634* (2013.01); *A61F 13/15658* (2013.01); *A61F 13/15764* (2013.01);
(Continued)

(58) Field of Classification Search
CPC .................. B05C 19/04; A61F 13/535; A61F 2013/530591; A61F 13/5323; A61F 2013/53051; A61F 2013/530518
See application file for complete search history.

(56) References Cited

U.S. PATENT DOCUMENTS 4,005,957 A    2/1977  Savich
4,392,908 A    7/1983  Dehnel
(Continued)

FOREIGN PATENT DOCUMENTS

CN    1406566 A    4/2003
CN    1853013 A    10/2006
(Continued)

OTHER PUBLICATIONS

Baer, Samuel C. PhD, Particle Containment and Immobilization in Roll Good Materials, INJ, Fall 2004, pp. 54-59.
(Continued)

*Primary Examiner* — Scott W Dodds
(74) *Attorney, Agent, or Firm* — Kimberly-Clark Worldwide, Inc.

(57) ABSTRACT

Pulpless absorbent cores and methods of manufacture are disclosed. A method of forming a pulpless absorbent core may comprise moving a foraminous forming surface having un-masked portions and masked portions in a machine direction, the un-masked portions defining an absorbent core region. The method may further comprise depositing particulate material at a velocity of less than 1200 meters per minute in the absorbent core region while applying a vacuum. The absorbent core region may comprise: a front core region spanning a first half of the absorbent core region and a rear core region spanning a second half, wherein the front core region trails the rear core region in the machine direction, and the masked portions of the foraminous forming surface block airflow through the forming surface to cause greater than 60% of the particulate material deposited in the absorbent core region to locate in the front core region.

9 Claims, 20 Drawing Sheets

(51) Int. Cl.
*A61F 13/535* (2006.01)
*B32B 5/16* (2006.01)
*B32B 7/12* (2006.01)
*A61F 13/53* (2006.01)

(52) U.S. Cl.
CPC ...... *A61F 13/15804* (2013.01); *A61F 13/535* (2013.01); *B32B 5/16* (2013.01); *B32B 7/12* (2013.01); *A61F 2013/15943* (2013.01); *A61F 2013/530481* (2013.01); *A61F 2013/530802* (2013.01); *A61F 2013/53908* (2013.01); *B32B 2307/726* (2013.01); *B32B 2555/02* (2013.01)

(56) References Cited

U.S. PATENT DOCUMENTS

| | | | |
|---|---|---|---|
| 4,585,448 | A | 4/1986 | Enloe |
| 4,679,704 | A | 7/1987 | Dunlop et al. |
| 4,764,325 | A | 8/1988 | Angstadt |
| 5,017,324 | A | 5/1991 | Kaiser et al. |
| 5,028,224 | A | 7/1991 | Pieper et al. |
| 5,028,225 | A | 7/1991 | Staheli |
| 5,213,817 | A | 5/1993 | Pelley |
| 5,279,854 | A | 1/1994 | Kendall et al. |
| 5,415,716 | A | 5/1995 | Kendall |
| 5,429,788 | A | 7/1995 | Ribble et al. |
| 5,447,677 | A | 9/1995 | Griffoul et al. |
| 5,494,622 | A | 2/1996 | Heath et al. |
| 5,514,324 | A | 5/1996 | Bachar |
| 5,516,569 | A | 5/1996 | Veith et al. |
| 5,750,066 | A | 5/1998 | Vonderhaar et al. |
| 5,763,331 | A | 6/1998 | Demhartner |
| 5,766,388 | A | 6/1998 | Pelley et al. |
| 5,983,457 | A | 11/1999 | Toney et al. |
| 6,080,909 | A | 6/2000 | Osterdahl et al. |
| 6,093,474 | A | 7/2000 | Sironi |
| 6,162,959 | A | 12/2000 | O'Connor |
| 6,330,735 | B1 | 12/2001 | Hahn et al. |
| 6,403,857 | B1 | 6/2002 | Gross et al. |
| 6,459,016 | B1 | 10/2002 | Rosenfeld et al. |
| 6,664,439 | B1 | 12/2003 | Arndt et al. |
| 6,703,846 | B2 | 3/2004 | Delzer et al. |
| 6,706,129 | B2 | 3/2004 | Ando et al. |
| 6,932,929 | B2 | 8/2005 | Krautkramer et al. |
| 6,972,011 | B2 | 12/2005 | Maeda et al. |
| 7,121,818 | B2 | 10/2006 | Driskell |
| 7,527,823 | B2 | 5/2009 | Tombült-Meyer et al. |
| 7,717,150 | B2 | 5/2010 | Manabe et al. |
| 7,872,168 | B2 | 1/2011 | Sawyer et al. |
| 7,906,065 | B1 | 3/2011 | Brown et al. |
| 7,938,813 | B2 | 5/2011 | Wang et al. |
| 8,148,598 | B2 | 4/2012 | Tsang et al. |
| 8,324,446 | B2 | 12/2012 | Wang et al. |
| 8,485,347 | B2 | 7/2013 | Jackels |
| 8,552,251 | B2 | 10/2013 | Zhou et al. |
| 8,852,381 | B2 | 10/2014 | Nhan et al. |
| 8,855,979 | B2 | 10/2014 | Blessing et al. |
| 8,960,122 | B2 | 2/2015 | Yano et al. |
| 9,033,018 | B2 | 5/2015 | Ogasawara et al. |
| 9,044,359 | B2 | 6/2015 | Wciorka et al. |
| 2002/0169430 | A1 | 11/2002 | Kirk et al. |
| 2003/0044562 | A1 | 3/2003 | Li et al. |
| 2003/0129915 | A1 | 7/2003 | Harriz |
| 2003/0130638 | A1* | 7/2003 | Baker ............... A61F 13/15626 604/368 |
| 2003/0134559 | A1 | 7/2003 | Delzer et al. |
| 2003/0212376 | A1 | 11/2003 | Walter et al. |
| 2003/0236510 | A1* | 12/2003 | Yasumura ......... A61F 13/15626 604/367 |
| 2006/0141891 | A1 | 6/2006 | Melius et al. |
| 2009/0018517 | A1 | 1/2009 | Cecconi et al. |
| 2010/0051166 | A1 | 3/2010 | Hundorf et al. |
| 2010/0228209 | A1 | 9/2010 | Carlucci et al. |
| 2010/0312208 | A1 | 12/2010 | Bond et al. |
| 2011/0041999 | A1 | 2/2011 | Hundorf et al. |
| 2011/0152809 | A1 | 6/2011 | Carlucci et al. |
| 2012/0024470 | A1 | 2/2012 | Hundorf et al. |
| 2012/0316523 | A1 | 12/2012 | Hippe et al. |
| 2012/0316524 | A1 | 12/2012 | Thomann et al. |
| 2012/0316528 | A1 | 12/2012 | Kreuzer et al. |
| 2013/0112348 | A1 | 5/2013 | Blessing et al. |
| 2013/0226119 | A1 | 8/2013 | Katsuragawa et al. |
| 2013/0240139 | A1 | 9/2013 | Zhou et al. |
| 2013/0331806 | A1 | 12/2013 | Rosati et al. |
| 2014/0005623 | A1 | 1/2014 | Wirtz et al. |
| 2014/0005625 | A1 | 1/2014 | Wirtz et al. |
| 2014/0027943 | A1 | 1/2014 | Hoshika |
| 2014/0163503 | A1 | 6/2014 | Arizti et al. |
| 2014/0163504 | A1 | 6/2014 | Bianchi et al. |
| 2014/0261987 | A1 | 9/2014 | Chartrel |
| 2014/0276509 | A1 | 9/2014 | Ducker et al. |
| 2014/0303582 | A1 | 10/2014 | Wright et al. |
| 2014/0308483 | A1 | 10/2014 | Li |
| 2014/0324008 | A1 | 10/2014 | Hundorf et al. |
| 2014/0329672 | A1 | 11/2014 | Colclough, Jr. et al. |
| 2015/0005727 | A1 | 1/2015 | Matsushita et al. |
| 2015/0011960 | A1 | 1/2015 | Arayama et al. |
| 2015/0065974 | A1 | 3/2015 | Michiels et al. |
| 2015/0080821 | A1 | 3/2015 | Peri et al. |
| 2015/0245952 | A1 | 9/2015 | Gahan |
| 2015/0245958 | A1 | 9/2015 | Chmielewski et al. |
| 2015/0359683 | A1 | 12/2015 | Jackels et al. |

FOREIGN PATENT DOCUMENTS

| | | |
|---|---|---|
| CN | 101070458 A | 11/2007 |
| CN | 103202746 A | 7/2013 |
| CN | 102281852 B | 8/2014 |
| CN | 104394823 B | 10/2017 |
| CN | 108779594 A | 11/2018 |
| EP | 0463716 B1 | 6/1999 |
| EP | 1110528 A2 | 6/2001 |
| EP | 0700673 B1 | 3/2002 |
| EP | 1253231 B1 | 11/2005 |
| EP | 1697057 B1 | 11/2007 |
| EP | 2532330 A1 | 12/2012 |
| EP | 2679210 B1 | 1/2015 |
| JP | 11320742 A2 | 11/1999 |
| WO | WO2007122525 A1 | 11/2007 |
| WO | WO2014145312 A2 | 9/2014 |

OTHER PUBLICATIONS

Industry News—Live from Index 2014, Ultrasonic diaper core former Helixbond, http://shows.nonwovens-industry.com/index2014/news/40624.

* cited by examiner

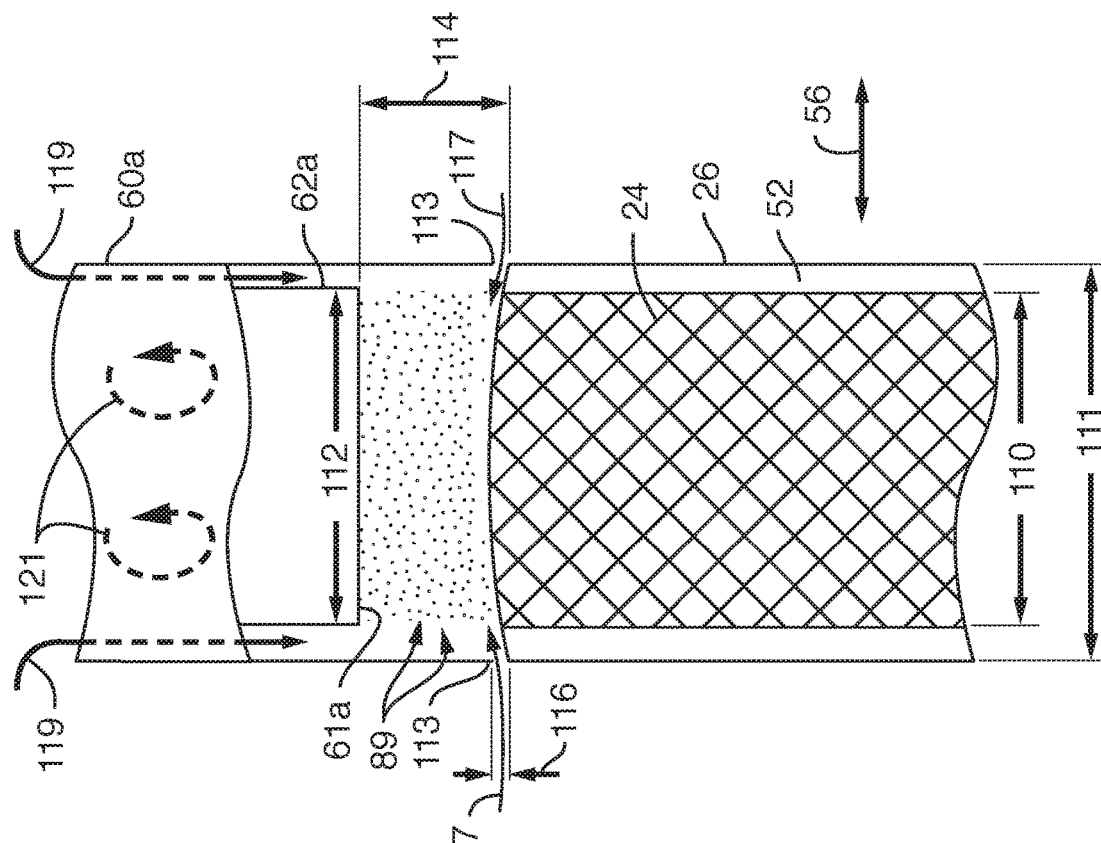
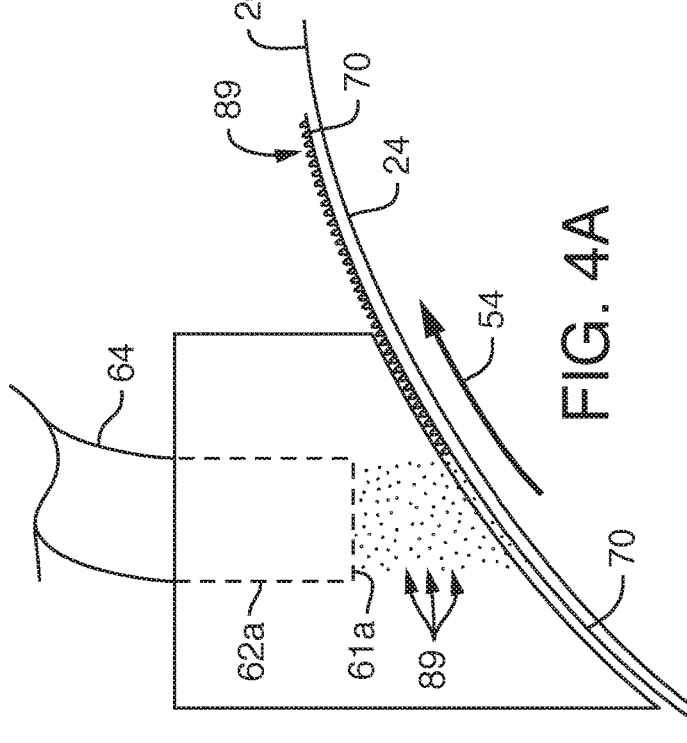
FIG. 4A
FIG. 4B

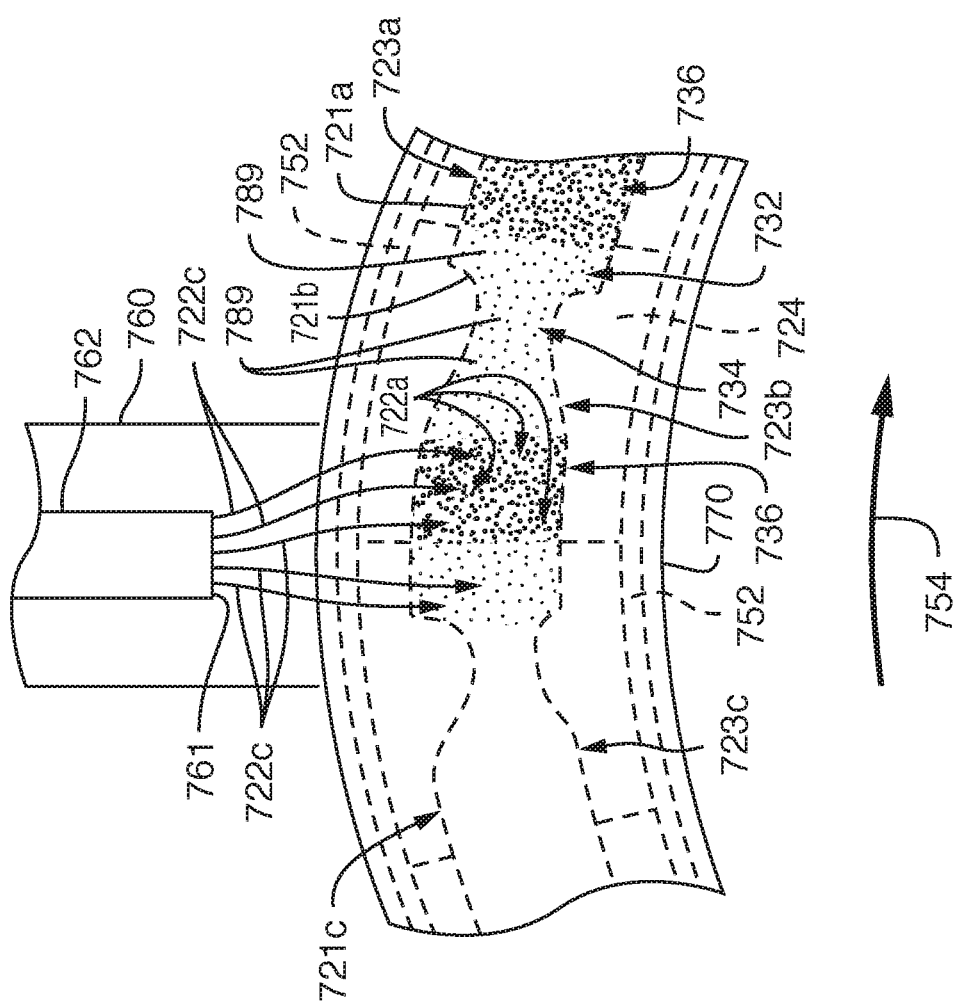

ABSORBENT CORES AND METHODS FOR FORMING ABSORBENT CORES

FIELD OF THE INVENTION

The field of this disclosure relates generally to absorbent cores and methods of manufacturing absorbent cores for use in absorbent articles, and more specifically to pulpless absorbent cores and methods of forming pulpless absorbent cores for use in absorbent articles, such as diapers, training pants, incontinence products, disposable underwear, medical garments, feminine care articles, absorbent swim wear, and the like.

BACKGROUND

Absorbent cores are used in different types of products to control and contain bodily fluids and other bodily liquid discharge. Many present absorbent cores include pulp fluff, or other cellulosic fibers, which act to absorb the discharged liquids. Present absorbent articles can also contain particulate material, for example superabsorbent material, mixed in with the cellulose fibers to greatly increase the absorbent capacity of the absorbent cores. In these instances, the cellulose fibers help to absorb discharged fluids and also to stabilize the superabsorbent material, for instance maintaining the location of the superabsorbent material within the absorbent cores. However, the presence of cellulose fibers in these absorbent cores imparts a significant amount of bulk to the absorbent cores. Accordingly, absorbent cores that have a high absorbent capacity and do not contain cellulose fibers, or do not contain a substantial amount of cellulose fibers, in order to reduce bulk may be desirable.

BRIEF SUMMARY OF THE INVENTION

This disclosure relates generally to absorbent cores and methods of manufacturing absorbent cores for use in absorbent articles, and more specifically to pulpless absorbent cores and methods of forming pulpless absorbent cores for use in absorbent articles, such as diapers, training pants, incontinence products, disposable underwear, medical garments, feminine care articles, absorbent swim wear, and the like.

In a first embodiment, a method of forming a pulpless absorbent core may comprise moving a foraminous forming surface in a machine direction, the foraminous forming surface having un-masked portions and masked portions, and wherein the un-masked portions define an absorbent core region of the foraminous forming surface, and depositing particulate material at a velocity of less than 1200 meters per minute through a particulate material inlet and at the foraminous forming surface in the absorbent core region while applying a vacuum to the foraminous forming surface. The absorbent core region may comprise: a front core region spanning a first half of the absorbent core region and a rear core region spanning a second half of the absorbent core region, and the front core region may trail the rear core region in the machine direction. Additionally, the masked portions of the foraminous forming surface may block airflow through the foraminous forming surface to cause greater than 60% of the particulate material deposited in the absorbent core region to locate in the front core region.

Additionally, or alternatively, in further embodiments according to the first embodiment, the front core region may have an average basis weight that is between 110% and 170% of an average basis weight of the rear core region.

Additionally, or alternatively, in further embodiments according to any of the above embodiments according to the first embodiment, the front core region may an average basis weight that is between 125% and 150% of an average basis weight of the rear core region.

Additionally, or alternatively, in further embodiments according to any of the above embodiments according to the first embodiment, the masked portions of the foraminous forming surface block airflow through the foraminous forming surface to cause greater than 70% of the particulate material deposited in the absorbent core region to locate in the front core region.

Additionally, or alternatively, in further embodiments according to any of the above embodiments according to the first embodiment, the front core region may comprise the trailing half of the absorbent core region in the machine direction.

Additionally, or alternatively, in further embodiments according to any of the above embodiments according to the first embodiment, depositing particulate material at a velocity of less than 1200 meters per minute through a particulate material inlet and at the foraminous forming surface in the absorbent core region while applying a vacuum to the foraminous forming surface comprises depositing a first amount of particulate material at a velocity of less than 1200 meters per minute through a first particulate material inlet and at the foraminous forming surface in the absorbent core region while applying a vacuum to the foraminous forming surface, and the method may further comprise depositing a second amount particulate material at a velocity of less than 1200 meters per minute through a second particulate material inlet and at the foraminous forming surface in the absorbent core region while applying a vacuum to the foraminous forming surface.

Additionally, or alternatively, in further embodiments according to any of the above embodiments according to the first embodiment, the front core region may have an average basis weight between 200 gsm and 800 gsm, and the rear core region may have an average basis weight between 100 gsm and 600 gsm.

Additionally, or alternatively, in further embodiments according to any of the above embodiments according to the first embodiment, the method may further comprise depositing the particulate material at a velocity of less than 900 meters per minute through the particulate material inlet at the foraminous forming surface in the absorbent core region.

Additionally, or alternatively, in further embodiments according to any of the above embodiments according to the first embodiment, the method may further comprise depositing the particulate material at a velocity of less than 600 meters per minute through the particulate material inlet at the foraminous forming surface in the absorbent core region.

Additionally, or alternatively, in further embodiments according to any of the above embodiments according to the first embodiment, the method may further comprise mixing cellulose fibers with the particulate material before depositing the mixture of the cellulose fibers and the particulate material at the foraminous forming surface.

Additionally, or alternatively, in further embodiments according to any of the above embodiments according to the first embodiment, the cellulose fibers may comprise less than 10%, by weight, of an overall weight of the particulate material and the cellulose fibers deposited at the foraminous forming surface.

In a second embodiment, a method of forming a pulpless absorbent core may comprise moving a foraminous forming surface in a machine direction, the foraminous forming surface having un-masked portions and masked portions, and wherein the un-masked portions define an absorbent core region of the foraminous forming surface, and depositing particulate material at a velocity of less than 1200 meters per minute through a particulate material inlet and at the foraminous forming surface in the absorbent core region while applying a vacuum to the foraminous forming surface. In some embodiments, the absorbent core region may comprise: a front core region spanning a front third of the absorbent core region, a rear core region spanning a rear third of the absorbent core region, and a crotch region disposed between the front core region and the rear core region and spanning a middle third of the absorbent core region, where the front core region trails the rear core region in the machine direction. In some further embodiments the masked portions of the foraminous forming surface may block airflow through the foraminous forming surface to cause greater than 40% of the particulate material deposited in the absorbent core region to locate in the front core region.

Additionally, or alternatively, in further embodiments according to the second embodiment, the masked portions of the forming surface may comprise masked portions proximate the crotch region, the front core region of the may have a greatest cross-machine direction width, and the masked portions proximate the crotch region may extend inward from an edge of the absorbent core region between 10% and 40% of the greatest cross-machine direction width.

Additionally, or alternatively, in further embodiments according to any of the above embodiments according to the second embodiment, the masked portions of the forming surface may comprise masked portions proximate the crotch region, and the masked portions proximate the crotch region may comprise an area that is between 25% and 50% of an area defined by a greatest cross-machine direction width of the absorbent core region and a machine direction length of the absorbent core region.

Additionally, or alternatively, in further embodiments according to any of the above embodiments according to the second embodiment, depositing particulate material at a velocity of less than 1200 meters per minute through a particulate material inlet and at the foraminous forming surface in the absorbent core region while applying a vacuum to the foraminous forming surface comprises depositing a first amount of particulate material at a velocity of less than 1200 meters per minute through a first particulate material inlet and at the foraminous forming surface in the absorbent core region while applying a vacuum to the foraminous forming surface, and the method may further comprise depositing a second amount particulate material at a velocity of less than 1200 meters per minute through a second particulate material inlet and at the foraminous forming surface in the absorbent core region while applying a vacuum to the foraminous forming surface.

Additionally, or alternatively, in further embodiments according to any of the above embodiments according to the second embodiment, at least a portion of the absorbent core region may comprise an arcuate shape.

Additionally, or alternatively, in further embodiments according to any of the above embodiments according to the second embodiment, the front core region may have an average basis weight that is between 110% and 170% of an average basis weight of the rear core region.

Additionally, or alternatively, in further embodiments according to any of the above embodiments according to the second embodiment, the method may further comprise depositing the first amount of particulate material at a velocity of less than 900 meters per minute through the first particulate material inlet and onto the base carrier sheet absorbent core region, and depositing the second amount of particulate material at a velocity of less than 900 meters per minute through the second particulate material inlet and onto the base carrier sheet absorbent core region.

Additionally, or alternatively, in further embodiments according to any of the above embodiments according to the second embodiment, the method may further comprise depositing the particulate material at a velocity of less than 600 meters per minute through the particulate material inlet at the foraminous forming surface in the absorbent core region.

Additionally, or alternatively, in further embodiments according to any of the above embodiments according to the second embodiment, the method may further comprise mixing cellulose fibers with at least one of the first amount of particulate material and the second amount of particulate material before depositing the mixture of the cellulose fibers and the first amount of particulate material and/or the second amount of particulate material at the foraminous forming surface.

In a third embodiment, a method of forming an absorbent core may comprise advancing a base carrier sheet in a machine direction on a foraminous forming surface, the foraminous forming surface having un-masked portions and masked portions, and wherein the un-masked portions of the foraminous forming surface define an absorbent core region, applying a first adhesive onto a top surface of the base carrier sheet, advancing the base carrier sheet within a first particulate material delivery chamber, and depositing a first amount of particulate material at a velocity of less than 1200 meters per minute through a first particulate material inlet disposed within the first particulate material delivery chamber and at the foraminous forming surface in the absorbent core region while applying a vacuum to the foraminous forming surface. In some embodiments, the method may further comprise applying a second adhesive onto the first amount of particulate material outside of the first particulate material delivery chamber, advancing the base carrier sheet with the first adhesive, the first amount of particulate material, and the second adhesive into a second particulate material delivery chamber, depositing a second amount of particulate material at a velocity of less than 1200 meters per minute through a second particulate material inlet disposed within the second particulate material delivery chamber and at the foraminous forming surface in the absorbent core region while applying a vacuum to the foraminous forming surface, and applying a top carrier sheet over the second amount of particulate material. The absorbent core region may comprise a front core region spanning a first half of the absorbent core region and a rear core region spanning a second half of the absorbent core region, with the front core region trails the rear core region in the machine direction. Additionally, the masked portions of the foraminous forming surface may block airflow through the foraminous forming surface to cause greater than 60% of the particulate material deposited in the absorbent core region of the foraminous forming surface to locate in the front core region.

Additionally, or alternatively, in further embodiments according to the third embodiment, the front core region has an average basis weight between 200 gsm and 800 gsm, and wherein the rear core region has an average basis weight between 100 gsm and 600 gsm.

Additionally, or alternatively, in further embodiments according to any of the above embodiments according to the third embodiment, the front core region may have an average basis weight that is between 110% and 170% of an average basis weight of the rear core region.

Additionally, or alternatively, in further embodiments according to any of the above embodiments according to the third embodiment, the first adhesive may comprise a hot-melt adhesive, and the second adhesive may comprise a spray application aqueous binder (SAAB) adhesive.

Additionally, or alternatively, in further embodiments according to any of the above embodiments according to the third embodiment, the method may further comprise mixing cellulose fibers with at least one of the first amount of particulate material and the second amount of particulate material before depositing the mixture of the cellulose fibers and the first amount of particulate material and/or the second amount of particulate material at the foraminous forming surface.

Additionally, or alternatively, in further embodiments according to any of the above embodiments according to the third embodiment, the method may further comprise depositing at least one of the first amount of particulate material and the second amount of particulate material at a velocity of less than 900 meters per minute at the foraminous forming surface in the absorbent core region.

Additionally, or alternatively, in further embodiments according to any of the above embodiments according to the third embodiment, the method may further comprise depositing at least one of the first amount of particulate material and the second amount of particulate material at a velocity of less than 600 meters per minute at the foraminous forming surface in the absorbent core region.

Additionally, or alternatively, in further embodiments according to any of the above embodiments according to the third embodiment, at least some of the non-foraminous portions may extend inward from a greatest cross-machine direction extent of the foraminous portions between 5 cm and 15 cm.

Additionally, or alternatively, in further embodiments according to any of the above embodiments according to the third embodiment, the masked portions may comprise an area that is between 25% and 50% of an area defined by a greatest cross-machine direction width of the absorbent core region and a machine direction length of the absorbent core region.

Additionally, or alternatively, in further embodiments according to any of the above embodiments according to the third embodiment, least a portion of the absorbent core region may comprise an arcuate shape.

Additionally, or alternatively, in further embodiments according to any of the above embodiments according to the third embodiment, the non-foraminous portions may extend inward from a greatest cross-machine direction extent of the foraminous portions for a distance in the machine direction between 5 cm and 25 cm.

In a fourth embodiment, an absorbent core may comprise a front core region and a rear core region and particulate material spanning both the front core region and the rear core region. A basis weight of the absorbent core may also increase along a path from the rear core region to the front core region, and at least 60% of a particulate material content, by weight, of the absorbent core may be located in the front core region.

Additionally, or alternatively, in further embodiments according to the fourth embodiment, at least 70% of the particulate material, by weight, in the absorbent core may be located in the front core region.

Additionally, or alternatively, in further embodiments according to any of the above embodiments according to the fourth embodiment, the basis weight of the absorbent core may increase at a linear rate along the path from the rear core region to the front core region.

Additionally, or alternatively, in further embodiments according to any of the above embodiments according to the fourth embodiment, each of the front core region and the rear core region may span half of a length of the absorbent core.

Additionally, or alternatively, in further embodiments according to any of the above embodiments according to the fourth embodiment, the absorbent article may further comprise a crotch region disposed between the rear core region and the front core region, and each of the front core region, the crotch region, and the rear core region span a third of a length of the absorbent core.

Additionally, or alternatively, in further embodiments according to any of the above embodiments according to the fourth embodiment, the absorbent article may further comprise cellulose fibers intermixed with the particulate material.

Additionally, or alternatively, in further embodiments according to any of the above embodiments according to the fourth embodiment, the cellulose fibers may comprise less than 10% of an overall weight of the absorbent core.

Additionally, or alternatively, in further embodiments according to any of the above embodiments according to the fourth embodiment, the absorbent article may further comprise both hot-melt adhesive and spray-application aqueous binder (SAAB) adhesive.

Additionally, or alternatively, in further embodiments according to any of the above embodiments according to the fourth embodiment, an average basis weight of the absorbent core in the rear core region may be between 100 and 600 gsm.

Additionally, or alternatively, in further embodiments according to any of the above embodiments according to the fourth embodiment, an average basis weight of the absorbent core in the crotch region may be between 150 and 700 gsm.

Additionally, or alternatively, in further embodiments according to any of the above embodiments according to the fourth embodiment, an average basis weight of the absorbent core in the front core region may be between 200 and 800 gsm.

Additionally, or alternatively, in further embodiments according to any of the above embodiments according to the fourth embodiment, the crotch region may include two wide end regions and a narrow central region.

Additionally, or alternatively, in further embodiments according to any of the above embodiments according to the fourth embodiment, the crotch region of the absorbent core may comprise a first end region, a central region, and a second end region, and a smallest cross-direction dimension of each of the first end region and the second end region may be greater than a smallest cross-direction dimension of the central region Additionally, or alternatively, in further embodiments according to any of the above embodiments according to the fourth embodiment, an area of the rear core region is greater than an area of the crotch region.

Additionally, or alternatively, in further embodiments according to any of the above embodiments according to the fourth embodiment, an area of the front core region is greater than an area of the rear core region.

In a fifth embodiment, an absorbent core may comprise a front core region, a crotch region, and a rear core region, and particulate material located in each of the front core region, the crotch region, and the rear core region. An average basis weight of the absorbent core in the rear core region may less than an average basis weight of the absorbent core in the crotch region, and the average basis weight of the absorbent core in the crotch region may be less than an average basis weight of the absorbent core in the front core region.

Additionally, or alternatively, in further embodiments according to the fifth embodiment, the average basis weight of the absorbent core in the rear core region may be between 100 gsm and 600 gsm.

Additionally, or alternatively, in further embodiments according to any of the above embodiments according to the fifth embodiment, the average basis weight of the absorbent core in the crotch region may be between 150 and 700 gsm.

Additionally, or alternatively, in further embodiments according to any of the above embodiments according to the fifth embodiment, the average basis weight of absorbent core in the front core region may be between 200 and 800 gsm.

Additionally, or alternatively, in further embodiments according to any of the above embodiments according to the fifth embodiment, each of the front core region, the crotch region, and the rear core region may span a length that is one-third of an overall length of the absorbent core.

Additionally, or alternatively, in further embodiments according to any of the above embodiments according to the fifth embodiment, the crotch region may include two wide end regions and a narrow central region.

Additionally, or alternatively, in further embodiments according to any of the above embodiments according to the fifth embodiment, the crotch region of the absorbent core may comprise a first end region, a central region, and a second end region, and a smallest cross-direction dimension of each of the first end region and the second end region may be greater than a smallest cross-direction dimension of the central region Additionally, or alternatively, in further embodiments according to any of the above embodiments according to the fifth embodiment, an area of the rear core region may be greater than an area of the crotch region.

Additionally, or alternatively, in further embodiments according to any of the above embodiments according to the fifth embodiment, an area of the front core region may be greater than an area of the rear core region.

Additionally, or alternatively, in further embodiments according to any of the above embodiments according to the fifth embodiment, the absorbent article may further comprise cellulose fibers intermixed with the particulate material.

Additionally, or alternatively, in further embodiments according to any of the above embodiments according to the fifth embodiment, the cellulose fibers may comprise less than 10% of an overall weight of the absorbent core.

Additionally, or alternatively, in further embodiments according to any of the above embodiments according to the fifth embodiment, at least 60% of the total particulate material content, by weight, in the absorbent core may be located in the front core region.

Additionally, or alternatively, in further embodiments according to any of the above embodiments according to the fifth embodiment, the average basis weight of the absorbent core may increase at a linear rate along a path from the rear core region to the front core region.

Additionally, or alternatively, in further embodiments according to any of the above embodiments according to the fifth embodiment, each of the front core region, the crotch region, and the rear core region may span a third of a length of the absorbent core.

Additionally, or alternatively, in further embodiments according to any of the above embodiments according to the fifth embodiment, the absorbent article may further comprise both hot-melt adhesive and spray-application aqueous binder (SAAB) adhesive.

BRIEF DESCRIPTION OF THE DRAWINGS

FIG. 4A is a side view of an exemplary particulate absorbent material delivery chamber that may be used in the assembly of FIG. 1.

FIG. 4B is a front view of an exemplary particulate absorbent material delivery chamber that may be used in the assembly of FIG. 1.

FIG. 16B is another internal view of the exemplary particulate absorbent material delivery conduit of FIG. 16A where the base carrier sheet has advanced further through the exemplary particulate absorbent material delivery conduit.

DETAILED DESCRIPTION OF THE DRAWINGS

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Moreover, the use of "top", "bottom", "above", "below" and variations of these terms is made for convenience, and does not require any particular orientation of the components.

Figure 1:
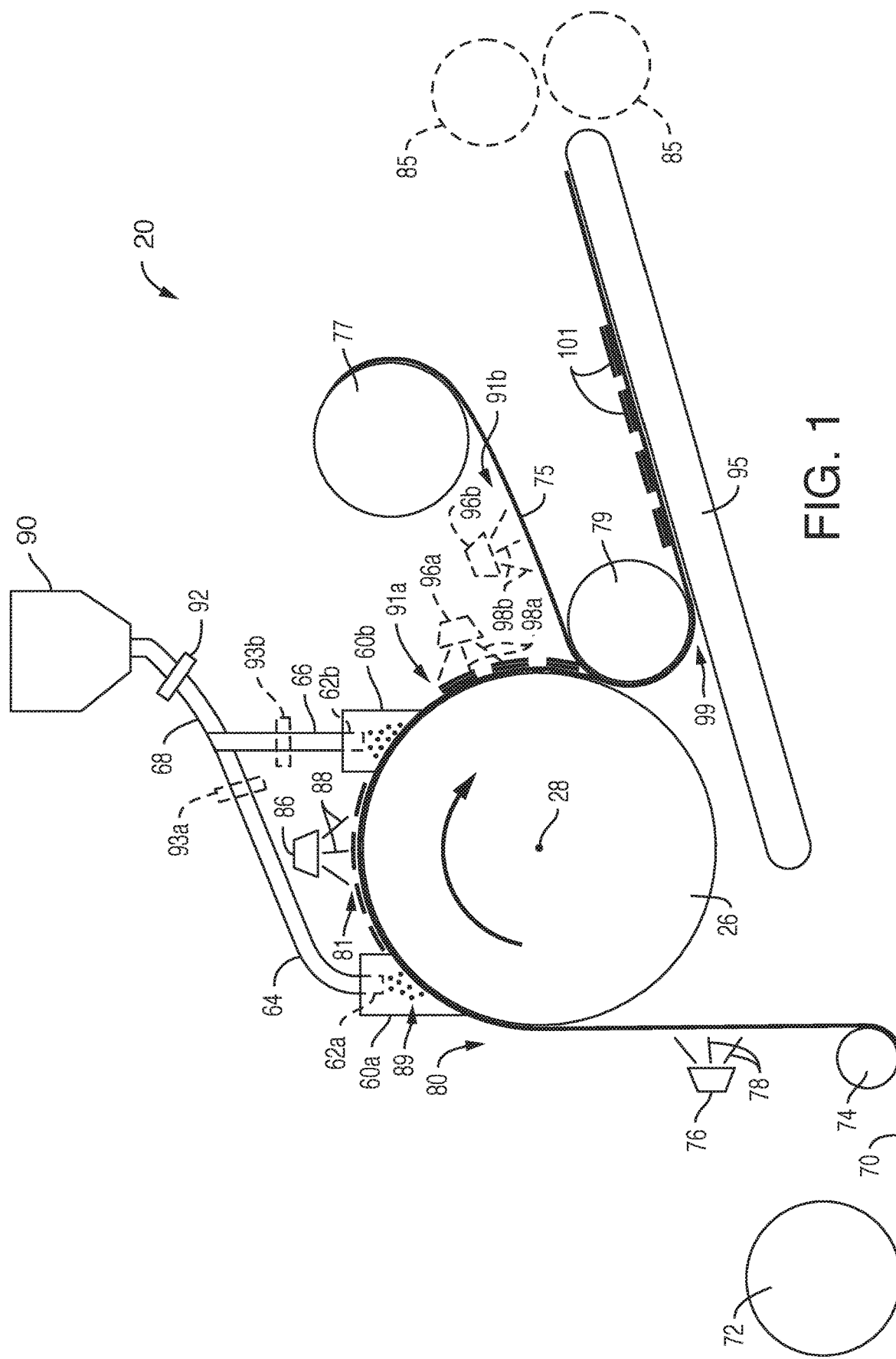
FIG. 1 is a schematic of an example forming assembly for forming absorbent cores.

With reference now to the drawings, FIG. 1 depicts a schematic drawing of an example absorbent core forming apparatus 20, which may be used to form absorbent cores. A few components of apparatus 20 include the forming drum 26 and the particulate material delivery chambers 60a, 60b. Accordingly, in some embodiments, apparatus 20 may be used to form absorbent cores comprising particulate material. Superabsorbent material (SAM) is one example of particulate material contemplated by this disclosure. In at least some of these embodiments, the particulate material content of the formed absorbent cores may comprise the majority, by weight, of the contents of the absorbent cores. In other embodiments, the particulate material content of the formed absorbent cores may comprise between 90%-100%, by weight, of the contents of the absorbent cores. These absorbent cores may be described herein as pulpless absorbent cores. As used herein, the phrase pulpless absorbent cores may include both absorbent cores that are truly pulpless and absorbent cores that are only substantially pulpless which have cellulose fibers comprising between 0.5%-10%, by weight, of the total contents of the absorbent cores. Pulpless cores may have one or more advantages relative to absorbent cores that have higher cellulose fiber content. For example, pulpless cores can have absorbent properties, such as absorbent capacity, similar to cores with higher cellulose fiber content. However, pulpless cores can have smaller dimensions than cores having cellulose fiber pulp content. In particular, the pulpless cores may have a reduced thickness in comparison to cores with higher cellulose fiber content.

In the exemplary embodiment of FIG. 1, a base carrier sheet 70 may be unwound from a carrier sheet roll 72. One or more material handling rollers 74 may be used to transport the base carrier sheet 70 proximate forming drum 26. Once in proximity to forming drum 26, the base carrier sheet 70 may be drawn to forming drum 26 by vacuum pressure, described in more detail below in relation to FIGS. 2 and 3. The forming drum 26 rotates in the direction of arrow 10, about drive-shaft 28, advancing the base carrier sheet 70 through one or more absorbent core forming stages, ultimately resulting in the absorbent cores 101. Although absorbent cores 101 are shown as discrete pads, in other embodiments, absorbent cores 101 may be formed as a continuous ribbon.

In some embodiments, the base carrier sheet 70 may comprise a nonwoven material such as a meltblown, spunbond-meltblown-spunbond (SMS), spunlace material, or a natural tissue material. However, in other embodiments, any suitable non-woven material may be used. The base carrier sheet 70 should be at least semi-permeable to air-flow. For instance, the base carrier sheet 70 should be sufficiently permeable such that air is be able to move through the base carrier sheet 70 from a top surface disposed away from the forming surface 24 to a bottom surface disposed proximate the forming surface 24, and ultimately through forming surface 24 into the interior of forming drum 26. Some example suitable dimensions of the base carrier sheet 70 include a width between about 7 cm to about 36 cm. Some example suitable basis weights for the base carrier sheet 70 range from about 5 grams per square meter (gsm) to about 50 gsm. However, the specific dimensions and basis weights used for the base carrier sheet 70 may differ, even outside of these ranges, based on the specific application or desired properties for the absorbent cores 101.

In the example of FIG. 1, the base carrier sheet 70 first moves through first adhesive application zone 80, where adhesive applicator 76 applies adhesive 78 to the base carrier sheet 70. In some examples, the adhesive 78 may be a hot-melt adhesive, such as either a contact hot-melt adhesive or a non-contact hot-melt adhesive. Although, in other examples, adhesive 78 may be any other suitable adhesive for application on a carrier sheet. Further, adhesive 78 may be applied using any suitable application technique or techniques. For instance, adhesive 78 may be applied with a spray application, with a slot-coat application, or by any other appropriate application technique.

After exiting first adhesive application zone 80, the base carrier sheet 70, now containing adhesive 78, is brought in proximity to forming drum 26, where the base carrier sheet 70 is drawn to the forming drum through vacuum pressure. The base carrier sheet then enters particulate material delivery chamber 60a. Inside of particulate material delivery chamber 60a, particulate material may be deposited onto the base carrier sheet 70. More specifically, the particulate material may be deposited onto adhesive 78, where the particulate material becomes stabilized, or immobilized on the base carrier sheet 70, by adhesive 78.

The hopper 90 in FIG. 1 may contain particulate material that is delivered to the particulate material delivery chambers 60a, 60b. The connecting pipe 68 may connect directly to the hopper 90 in order to transport the particulate material from the hopper 90 to the particulate material delivery chambers 60a, 60b. In at least some embodiments, the connecting pipe 68 may include metering device 92. The metering device 92 may be any sort of bulk material metering device, based on volumetric, gravimetric, or mass flow principles, or the like. The metering device 92 may ensure that only a specified amount (for instance, by volume or by weight) of particulate material flows through the connecting pipe per unit of time. Some example suitable ranges for the volume of particulate material flowing through the metering device 92 are between about 5,000 grams per minute (g/min) and about 25,000 g/min. In this manner, the metering device 92 can help to ensure a proper amount of particulate material is delivered to particulate material delivery chambers 60a, 60b.

In the example shown in FIG. 1, the connecting pipe 68 may split into delivery pipes 64 and 66. Each of the delivery pipes 64 and 66 may enter the particulate material delivery chambers 60a, 60b, forming particulate material delivery conduits 62a, 62b. The particulate material delivered to the particulate material delivery chambers 60a, 60b may exit the particulate material delivery conduits 62a, 62b and be deposited onto the adhesive 78 and the base carrier sheet 70. In some alternative embodiments, instead of a single metering device 92, multiple metering devices may be used to ensure proper delivery of particulate material to each of the particulate material delivery chambers 60a, 60b. For example, each of the delivery pipes 64 and 66 may include a metering device, represented by the dashed boxes 93a and 93b in FIG. 1, instead the apparatus 20 including metering device 92.

After exiting the particulate material delivery chamber 60a, the base carrier sheet 70, now containing adhesive 78 and particulate material, may enter second adhesive application zone 81. In some embodiments, second adhesive application zone 81 may be similar to first adhesive application zone 80. For example, in second adhesive application zone 81, adhesive applicator 86 may apply adhesive 88 to the base carrier sheet 70. More specifically, adhesive applicator 86 may apply adhesive 88 onto the particulate material that is stabilized on the base carrier sheet 70. In some embodiments, adhesive 88 may be the same as adhesive 78. For instance, adhesive 88 may also be a hot-melt adhesive, such as a non-contact hot-melt adhesive. Adhesive 88 may also be applied to the base carrier sheet 70 in a similar manner as adhesive 78 was applied to the base carrier sheet 70, such as with a spray application. Although, in other embodiments, adhesive 88 may be a different type of adhesive than adhesive 78 and/or may be applied in a different manner than adhesive 78.

In still other embodiments, adhesive 88 may not be a hot-melt adhesive. In some embodiments, adhesive 88 may be a spray-application aqueous binder (SAAB) adhesive. Where adhesive 88 is a SAAB adhesive, adhesive 88 may be applied with a spray-application. Implementing adhesive 88 as a SAAB adhesive may be preferable in certain embodiments, as SAAB adhesives may be able to better penetrate particulate material than hot-melt adhesives, thereby allowing for greater stabilization of the particulate material deposited onto the base carrier sheet 70.

After passing through second adhesive application zone 81, the base carrier sheet 70 now includes a first adhesive, adhesive 78, disposed on the base carrier sheet 70, a first amount of particulate material 89 (as can be seen in further detail in FIG. 6A) disposed on the adhesive 78, and a second adhesive, adhesive 88, disposed on the first amount of particulate material. The base carrier sheet 70 then enters the particulate material delivery chamber 60b. In the particulate material delivery chamber 60b, a second amount of particulate material is deposited onto adhesive 88 in a similar manner as particulate material was deposited onto adhesive 78 in the particulate delivery chamber 60a.

In some embodiments, the particulate material delivered to the base carrier sheet 70 in the particulate material delivery chambers 60a, 60b may be the same type of particulate material. In other embodiments, however, the type of particulate material delivered to the base carrier sheet 70 in the particulate material delivery chamber 60a may be different than the type of particulate material delivered to the base carrier sheet 70 in the particulate material delivery chamber 60b. In such embodiments, apparatus 20 may have two separate hoppers that each store different types of particulate material, in contrast to the example of FIG. 1. Additionally, separate connecting and delivery pipes may connect to each of the hoppers and to each of the particulate material delivery chambers 60a, 60b to maintain separation of the different particulate material types. Alternatively, apparatus 20 may still include only the single hopper 90 and the connecting and delivery pipes 68, 64, and 66, as shown in FIG. 1. In such embodiments, the hopper 90 may have two separate internal compartments to maintain separation of the different particulate material types. Additionally, connecting pipe 68 may include separate internal lumens. A first of the internal lumens may connect to a first internal compartment of the hopper 90 and to delivery pipe 64, while a second of the internal lumens may connect to a second internal compartment of the hopper 90 and to delivery pipe 66.

As mentioned previously, in some embodiments the particulate material may comprise superabsorbent material (SAM). Suitable superabsorbent materials are well known in the art and are readily available from various suppliers. Example suitable superabsorbent materials may include BASF 9700, available from BASF Corporation, a business having offices located in Charlotte, N.C., U.S.A; and Evonik 5600, available from Evonik Industries, a business having offices located in Parsippany, N.J., U.S.A.

In other embodiments, the particulate material may comprise low- or non-absorbent material such as charcoal, sugar (e.g. xylitol or the like), or encapsulated material. Accordingly, this disclosure contemplates in any of the disclosed embodiments that the delivered particulate material may be either an absorbent material, a non-absorbent material, or both. For instance, absorbent particulate material may be mixed with non-absorbent particulate material, or a first of the particulate material delivery chambers 60a, 60b may deliver absorbent particulate material and a second of the particulate material delivery chambers 60a, 60b may deliver non-absorbent particulate material.

Once the second amount of particulate material has been deposited onto the base carrier sheet 70, a top carrier sheet 75 may be applied onto the second amount of particulate material. The top carrier sheet 75 may be unwound from a roll 77 of top carrier sheet material, and may be transported proximate the forming drum 26 via one or more material handling rollers 79. After the top carrier sheet 75 has been applied onto the second amount of particulate material, the edges of the top carrier sheet 75 and the base carrier sheet 70 may be bonded together (not shown) to form the pulpless absorbent cores 101. The absorbent cores 101 may then be transported on conveyer 95 for further processing.

In some embodiments, material handling roller 79 may also perform a function similar to a nip roller. For instance, material handling roller 79 may come into close proximity to conveyer 95 in region 99 and the absorbent core 101 may be compressed to reduce bulk and/or to more securely bond the portions of the absorbent core 101 together. In other embodiments, however, one or more separate rollers may perform a nip function, such as rollers 85.

In some alternative embodiments, a third adhesive may be applied to the second amount of particulate material before the top carrier sheet 75 is applied to the second amount of particulate material. In some of these embodiments, apparatus 20 may further include third adhesive application zone 91a. Where apparatus 20 includes third adhesive application zone 91a, adhesive applicator 96a may apply adhesive 98a to the second amount of particulate material before the top carrier sheet 75 is applied. In various embodiments, adhesive 98a may be similar to either adhesive 78 or adhesive 88 described previously, and may be applied in any of the previously described methods. In different embodiments, however, apparatus 20 may include third adhesive application zone 91b instead of third adhesive application zone 91a. In these embodiments, adhesive applicator 96b may apply adhesive 98b directly to the top carrier sheet 75, instead of onto the second amount of particulate material. Additionally, adhesive 98b may be similar to either adhesive 78 or adhesive 88 described previously, except that adhesive 98b may not be a SAAB adhesive, as SAAB adhesives may not be suitable for direct application to carrier sheets. Further, adhesive 98a may be applied in any of the previously described methods. This third adhesive, applied by either adhesive applicator 96a or adhesive applicator 96b, may further help to stabilize the second amount of particulate material and/or to more securely attach the top carrier sheet 75 to the second amount of particulate material.

The adhesive applicators 76, 86, and/or 96a or 96b may be configured to apply adhesive in a continuous manner in some embodiments. In other embodiments, however, the adhesive applicators 76, 86, and/or 96a or 96b may be configured to apply adhesive in an intermittent fashion. For instance, the adhesive applicators 76, 86, and/or 96a or 96b may be applied intermittently to target zones on the base carrier sheet 70 to help stabilize the particulate material at locations on the base carrier sheet that will be most effective in absorbing liquid in the resulting absorbent cores due to the placement of the absorbent cores within an absorbent article.

Additionally, in at least some embodiments, the adhesive applicators 76, 86, and/or 96a or 96b may apply adhesive in a coordinated, intermittent fashion. In these embodiments, the adhesive applicator 86 may apply adhesive intermittently in a fashion such that the adhesive applicator 86 applies adhesive on top of the adhesive applied by adhesive applicator 76. After application of adhesive by the adhesive applicator 86, the adhesive applied by the adhesive applicator 86 would overlay the adhesive applied by the adhesive applicator 76. In embodiments that include adhesive applicator 96a or 96b, the adhesive applicator 96a or 96b may apply adhesive in an intermittent fashion such that the adhesive applied by the adhesive applicator 96a or 96b overlays the adhesive applied by the adhesive applicator 76 and the adhesive applied by the adhesive applicator 86.

Figure 2:
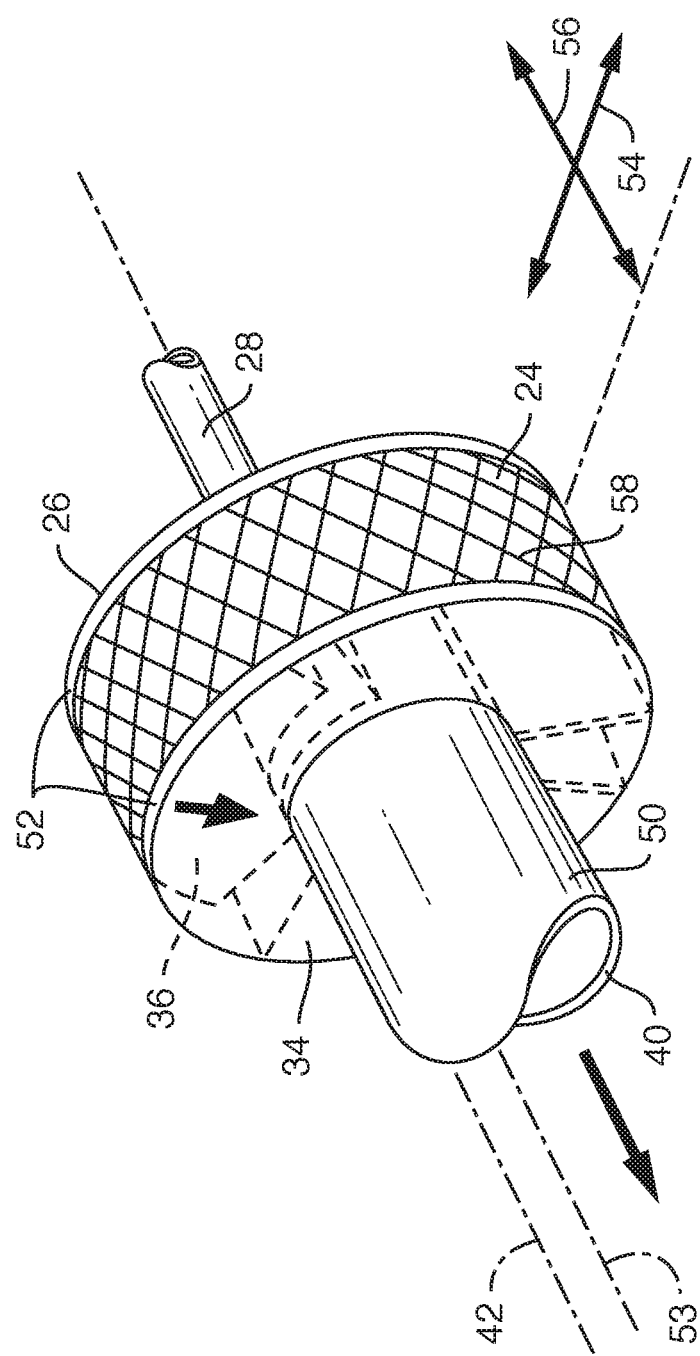
FIG. 2 is a perspective view of an exemplary forming drum that may be used in the assembly of FIG. 1.
Figure 3:
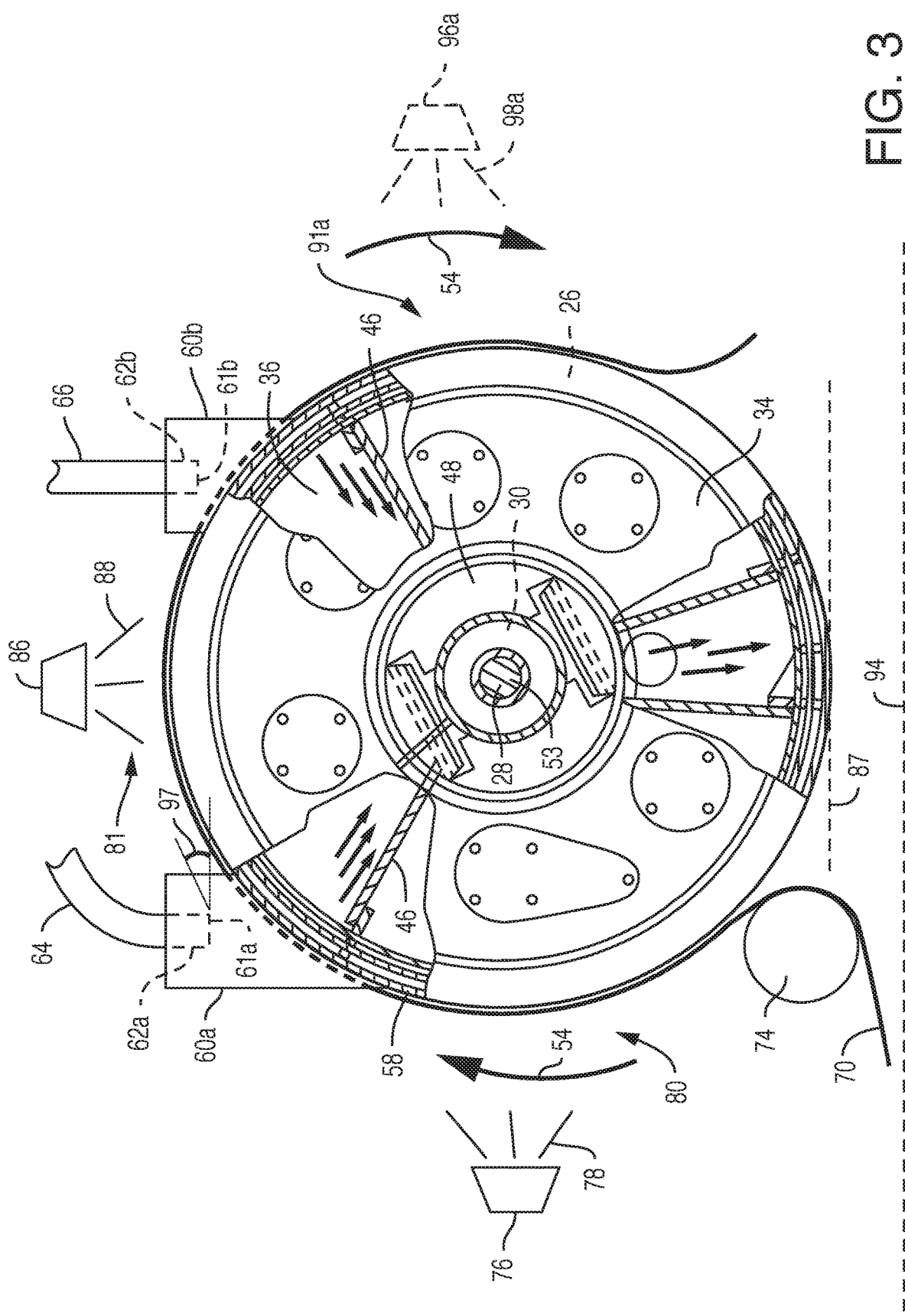
FIG. 3 is a side view of an example forming drum and associated components that may be used in the assembly of FIG. 1.

FIGS. 2 and 3 more closely depict portions of apparatus 20, including forming drum 26. The forming drum 26 includes a movable, foraminous forming surface 24, indicated by the hatched pattern in FIG. 2, extending around the circumference of the forming drum 26. The forming drum 26 is mounted on a drive shaft 28 and supported by bearings 30 (as can be seen in FIG. 3). The forming drum 26 includes a circular drum wall (not shown) operatively connected to and rotated by the drum drive shaft 28. The shaft 28 is driven in rotation by a suitable motor or line shaft (not shown) in a clockwise direction as depicted by the arrows in FIG. 3. In some embodiments, the drum wall can be a primary, load-bearing member, and the drum wall can extend generally radially and circumferentially about the drum drive shaft 28.

A vacuum duct 36 located radially inwardly of the forming surface 24 extends over an arc of the interior of the forming drum 26. The vacuum duct 36 is in fluid communication with the forming surface 24 for drawing air through the forming surface 24. The vacuum duct 36 is mounted on and in fluid communication with a vacuum supply conduit 40 connected to a vacuum source 42. The vacuum source 42 may be, for example, an exhaust fan and may create a vacuum within the forming drum which may be between about 2 inches of $H_2O$ to about 40 inches of $H_2O$. Beyond helping the base carrier sheet 70 adhere to the forming drum 26 as the base carrier sheet 70 advances around the forming drum, the vacuum pressure created by the vacuum source 42 may help to pull the particulate material exiting the particulate material delivery conduits 62a, 62b toward the forming surface 24. This vacuum pressure may help to spread the particulate material out on the forming surface 24 and to help form a more even distribution of the particulate material along the cross-machine direction 56 of the base carrier sheet 70.

The vacuum duct 36 is connected to the vacuum supply conduit 40 along an outer peripheral surface of the vacuum supply conduit 40, and extends circumferentially about at least a portion of the vacuum supply conduit 40. The vacuum duct 36 projects radially outwardly from the vacuum supply conduit 40 toward the forming surface 24 and includes axially spaced side walls 34 and angularly spaced end walls 46.

The shaft 28 extends through the drum wall and into the vacuum supply conduit 40 where it is received in the bearing 30. The bearing 30 is sealed with the vacuum supply conduit 40 so that air is not drawn in around the shaft 28 where it enters the vacuum supply conduit 40.

As representatively shown, the vacuum supply conduit 40 can include a conduit end wall 48 and a peripheral wall 50 that delimit the size and shape of the vacuum supply conduit 40. The vacuum supply conduit 40 can have any suitable cross-sectional shape. In the illustrated configuration, the vacuum supply conduit 40 has a generally circular cross-sectional shape. The vacuum supply conduit 40 can be operatively held in position with any suitable support structure. The support structure can also be joined and connected to further components or members that operatively support the portions of the vacuum supply conduit 40 structure that engage the drum drive shaft 28. For example, in the exemplary embodiment, one or more supports may connect to the bearing 30, and the entire vacuum supply conduit 40 may be supported by an overhead mount (not shown).

In the illustrated embodiment, walls 34 extend generally radially and circumferentially about the vacuum supply conduit 40. A drum rim 52 is joined to the walls 34 and is constructed and arranged to provide a substantially free movement of air through the thickness of the drum rim 52. The drum rim 52 is generally cylindrical in shape and extends along the direction of the drum axis 53, and circumferentially about the drum axis 53. As representatively shown, the drum rim 52 can be supported by and extend between the walls 34.

With reference to FIGS. 2 and 3, the forming surface 24 can be provided along the outer, cylindrical surface of the forming drum 26, and can extend along the axial and circumferential dimensions of the forming drum. The circumferential dimension is generally in a machine direction 54 and the axial dimension is generally in a cross-machine direction 56. The structure of the forming surface 24 can be composed of an assembly, and can include a foraminous member 58, which is operatively connected and joined to the forming drum 26. In some contemplated embodiments, the foraminous member 58 may be comprised of a system of multiple inserts. Exemplary foraminous members that may be used in conjunction with the present disclosure are further described in U.S. Pat. No. 6,630,088, titled "Forming media with enhanced air flow properties", filed on Oct. 23, 2000.

The forming surface 24 can be operatively held and mounted on the drum rim 52 by employing any suitable attachment mechanism. As one representative example, a system of nuts and bolts can be employed to secure the forming surface 24 onto an operative set of mounting rings. In such an example, the mounting rings can be operatively mounted on and secured to the drum rim 52. In other embodiments, the foraminous member 58 may be integral with forming drum 26.

Although not shown in FIG. 2, one or more masking plates may be attached to forming drum 26 on top of forming surface 24, as described in more detail below. The masking plates, for example, may be attached to drum rim 52, or alternately to the foraminous forming member 58. The masking plates may cover a portion of the forming surface 24 in order to block the vacuum in particular portions of the forming surface. The masking plates may allow for differently shaped absorbent cores to be formed on the forming drum 26, as will be explained in more detail below.

Suitable forming drum systems for use with the present disclosure are well known in the art. For example, see U.S. Pat. No. 4,666,647 entitled APPARATUS AND METHOD FOR FORMING A LAID FIBROUS WEB by K. Enloe et al. which issued May 19, 1987; and U.S. Pat. No. 4,761,258 entitled CONTROLLED FORMATION OF LIGHT AND HEAVY FLUFF ZONES by K. Enloe which issued Aug. 2, 1988; the entire disclosures of which are incorporated herein by reference in a manner that is consistent herewith. Other forming drum systems are described in U.S. Pat. No. 6,330,735, entitled APPARATUS AND PROCESS FOR FORMING A LAID FIBROUS WEB WITH ENHANCED BASIS WEIGHT CAPABILITY by J. T. Hahn et al. which issued Dec. 18, 2001, the entire disclosure of which is incorporated herein by reference in a manner that is consistent herewith. Systems for forming surfaces are described in U.S. Pat. No. 6,3630,088, entitled FORMING MEDIA WITH ENHANCED AIR FLOW PROPERTIES by Michael Barth Venturino et al. which issued Oct. 7, 2003, the entire disclosure of which is incorporated herein by reference in a manner that is consistent herewith.

With respect to FIG. 3, additional features of the particulate material delivery chambers 60a, 60b are evident. For instance, the particulate material delivery chambers 60a, 60b further depict the particulate material delivery conduits 62a, 62b terminating in inlets 61a, 61b. The inlets 61a, 61b, e.g. the plane of the opening of the particulate material delivery conduits 62a, 62b, may be positioned within the particulate material delivery chambers 60a, 60b such that the inlets 61a, 61b are generally parallel with ground 94 and/or with the base of the forming drum 87. In these embodiments, the particulate material delivered from the inlets 61a, 61b may exit the inlets 61a, 61b in a stream that is substantially perpendicular to the ground 94 and/or the base of the forming drum 87. Additionally, the particulate material delivery chambers 60a, 60b are both situated on the top half of the forming drum 26. In this configuration, the particulate material delivered from the particulate material delivery chambers 60a, 60b may fall with gravity towards the forming drum, instead of requiring additional energy to push the particulate material to the forming drum 26 against gravity.

However, in other embodiments, the inlets 61a, 61b may be tilted with respect to the ground 94 and/or the base of the forming drum 87. For instance, the inlets 61a, 61b may form an angle 97 with respect to the ground 94 and/or the base of the forming drum 87 (shown only with respect to inlet 61a in FIG. 3) having a value of between about 1 degree and about 45 degrees. In even further embodiments, the inlets 61a, 61b may form an angle 97 with respect to the ground 94 and/or the base of the forming drum 87 such that the inlets 61a, 61b are tangential to the forming drum 26.

FIGS. 4A and 4B depict different close-up views of particulate material delivery chamber 60a. FIG. 4A depicts a close-up of particulate material delivery chamber 60a as viewed in the machine direction 54. FIG. 4A further depicts individual particulate material particles 89 exiting inlet 61a of particulate material delivery conduit 62a and being deposited onto the base carrier sheet 70. The individual particulate material particles 89 can also be seen disposed and stabilized on the portion of the base carrier sheet 70 after the particulate material delivery chamber 60a in the machine direction 54.

As mentioned previously, the particulate material may be delivered through particulate material delivery conduit 62a from the hopper 90, which results in the particulate material being gravity fed to inlet 61a. In some embodiments, the individual particulate material particles 89 exiting inlet 61a may exit with a velocity that is less than 1200 meters per minute (m/min). In other embodiments, the individual particulate material particles 89 exiting inlet 61a may exit with a velocity that is less than 900 m/min. In still other embodiments, the individual particulate material particles 89 exiting inlet 61a may exit with a velocity that is less than 600 m/min. In yet other embodiments, the individual particulate material particles 89 exiting inlet 61a may exit with a velocity that is less than 300 m/min. These velocities are in contrast to particulate material that is introduced to a forming chamber pneumatically. Where particulate material is introduced pneumatically, the minimum possible introduction velocity is over 1200 m/min, because that is the velocity at which air needs to move in order to move particulate material particles. Accordingly, gravity feeding the particulate material into the particulate material delivery chamber 60a allows the individual particulate material particles 89 to be introduced proximate the forming drum 26 with a relatively lower velocity than if the particulate material were to be pneumatically introduced. This lower introduction velocity may allow the individual particulate material particles 89 to be influenced to a greater extent by the vacuum pressure of the forming drum 26. In this manner, the apparatus 20 may be able to achieve a more even distribution of the individual particulate material particles 89 on the base carrier sheet 70 throughout the cross-machine direction 56 than if the individual particulate material particles 89 we introduced into the particulate material delivery chamber 60a pneumatically.

FIG. 4B depicts an internal view of particulate material delivery chamber 60a as viewed from the cross-machine direction 56. As can be seen in FIG. 4B, the forming drum 26 may have a drum width 110, and the forming surface 24 may have a forming surface width 111. Generally, the drum width 110 will be greater than the forming surface width 111, as the forming drum 26 will include drum rim 52. However, this is not necessary in all embodiments. FIG. 4B also depicts the forming surface 24 as a relatively uniform and continuous surface. As mentioned previously, an as will be described in more detail below, in different embodiments one or more masking plates may obscure portions of the forming surface 24.

Also shown in FIG. 4B is the particulate material delivery conduit 62a and inlet 61a having an inlet width 112. In some embodiments, the inlet width 112 may be the same as the forming surface width 111. However, in other embodiments, the inlet width 112 may be smaller or greater than the forming surface width 111. For instance, the inlet width 112 may be the same as the drum width 110. In other examples, the inlet width 112 may smaller than the forming surface width 111, such as be between about one-quarter and about nine-tenths of the forming surface width 111. Additionally, inlet width 112 may be different for each of particulate material delivery conduits 62a, 62b.

The particulate material delivery conduit 62a may further having a vertical conduit spacing 114 comprising an amount of space between the inlet 61a of the particulate material delivery conduit 62a and the forming surface 24. In some examples, the vertical conduit spacing 114 may be between about 15 cm to about 100 cm.

As shown in FIG. 4B, the particulate material delivery chamber 60a may not be sealed against the forming drum 24. For instance, there may be a gap between the bottom edges 113 of the particulate material delivery chamber 60a and the forming surface 24 or the forming drum 26. The gap may have a gap space 116 that can be between about 0.5 cm and about 5 cm. In these embodiments, air may be able to enter into the particulate material delivery chamber 60*a* through gap space 116, as shown by arrows 117. Entry of air into the particulate material delivery chamber 60*a* may push the particulate material 89 toward a center of the forming surface 24 as the particulate material falls from the inlet 61*a* to the forming surface 24. This may result in a cross-direction 56 width of the particulate material 89 deposited at the forming surface 24 that is less than inlet width 112. This may result in more particulate material 89 present in a central region of formed absorbent cores than if there were no gap space 116. In some alternative embodiments, gap space 116 may not be disposed between the bottom edges 113 of the particulate material delivery chamber 60*a* and the forming surface 26. Rather, the bottom edges 113 of the particulate material delivery chamber 60*a* may be sealed against the forming drum 26, and a separate hole may be disposed through a side wall of the particulate material delivery chamber 60*a* to allow entry of air into the particulate material delivery chamber 60*a*.

Accordingly, in other embodiments, there may not be a gap space 116 between the bottom edges 113 of the particulate material delivery chamber 60*a* and the forming surface 24 or the forming drum 26. For instance, the bottom edges 113 of the particulate material delivery chamber 60*a* may contact the forming surface 24 or the forming drum 26, or one or more gap fillers (not shown) may be positioned to close up the gap space 116. In these embodiments, there may be no air entering gap space 116. Accordingly, there may be no air impinging on the stream of particulate material 89 and pushing the particulate material 89 inward from the edges of the forming surface 24. In these embodiments, the cross-direction 56 width of the particulate material 89 deposited at the forming surface 24 may be close or equal to the inlet width 112.

In some additional or alternative embodiments, an upper region of the particulate material delivery chamber 60*a* may be open and may allow air to flow into the particulate material delivery chamber 60*a* as shown by arrows 119. In these embodiments, the inflow of air may cause the particulate material 89 to fall toward the forming surface 24 in a more linear path. For instance, as air enters the particulate material delivery chamber 60*a*, the air may be pulled toward the forming surface 24 by the vacuum pressure in the chamber 60*a*, and may travel in a generally linear manner. The air may pull the particulate material 89 toward the forming surface 24, and the location of the particulate material 89 deposited at the forming surface 24 may be more heavily influenced by individual starting positions of the particulate material 89 at the inlet 61*a*.

However, in still other additional or alternative embodiments, an upper region of the particulate material delivery chamber 60*a* may be sealed and may prevent air from entering the particulate material delivery chamber 60*a*. In these embodiments, the air within the particulate material delivery chamber 60*a* may be more turbulent than in the embodiments where the upper region of the particulate material delivery chamber 60*a* allows entry of air, as represented by arrows 121. In these embodiments, the relatively greater turbulence may cause the particulate material 89 to fall in much less linear paths and, therefore, the location of the particulate material 89 deposited at the forming surface 24 may be less dependent on their initial starting position at the inlet 61*a* than where the upper region of the particulate material delivery chamber 60*a* is open to the air. In at least some of these embodiments, the resulting formed absorbent cores may have a relatively more even distribution of particulate material 89 throughout both the cross-machine direction 56 and the machine direction 54.

Although FIGS. 4A-B only depict particulate material delivery chamber 60*a*, it should be understood that particulate material delivery chamber 60*b* may be similar to the depicted particulate material delivery chamber 60*a*. However, it should also be understood that contemplated embodiments of the present disclosure include apparatuses including particulate material delivery chambers 60*a*, 60*b* that differ from each other. For instance, particulate material delivery chamber 60*a* may include a first set of features that were described above with respect to FIGS. 4A-B, while particulate material delivery chamber 60*b* includes a second, different set of features. As one illustrative example, particulate material delivery chamber 60*a* may include an inlet, e.g. inlet 61*a*, that is oriented generally parallel with respect to ground 94 and/or the base of the forming drum 87 while particulate material delivery chamber 60*b* may include an inlet, e.g. inlet 61*b*, that is oriented at an angle of 45 degrees with respect to ground 94 and/or the base of the forming drum 87. Of course, this is just one example. More generally, each of the particulate material delivery chambers 60*a*, 60*b* may include any of the features described above with respect to FIGS. 4A-B, and the specific set of features of each of particulate material delivery chambers 60*a*, 60*b* may not be the same.

Figure 5:
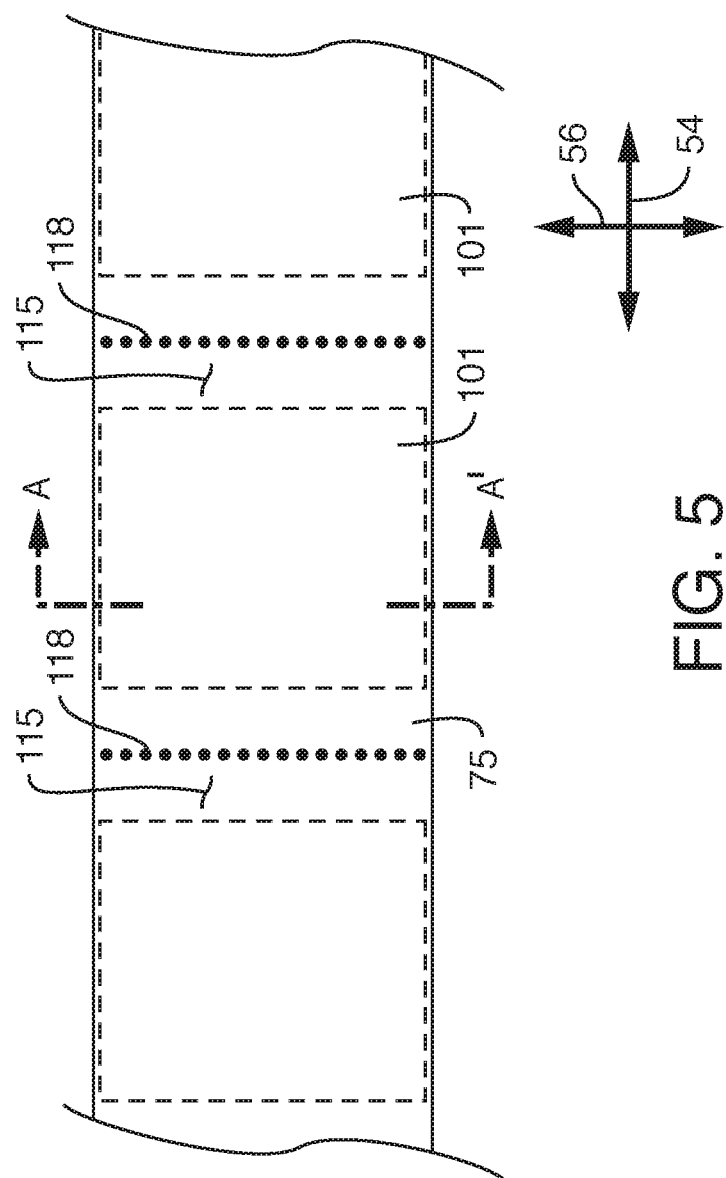
FIG. 5 is an illustration of an exemplary absorbent core structure that may be produced by the assembly of FIG. 1.

FIG. 5 depicts pulpless absorbent cores 101 as they may appear when exiting apparatus 20. In some examples, the absorbent cores 101 may be formed on a continuous carrier sheet, for instance the base carrier sheet 70 as shown in FIG. 1. As the base carrier sheet 70 including the various adhesives and particulate material exit off of the forming drum 26, another continuous carrier sheet, for instance the top carrier sheet 75, may be applied over the top of the base carrier sheet 70. In this manner, a continuous length of absorbent core may be formed by apparatus 20. However, as mentioned previously, in some embodiments, the forming surface 24 may include one or more masking members which may block a portion of the forming surface 24. In such embodiments, portions of the resulting length of the absorbent core may include gaps where there is no, or relatively little, particulate material content. These gaps are represented by gap regions 115 in FIG. 5. As the absorbent cores 101 were being formed on the forming surface 24, the applied vacuum would have been blocked by the masked portions of the forming surface such that little to no particulate material would have been drawn to the base carrier sheet 70 in gap regions 115. Accordingly, in such embodiments, discrete absorbent cores 101 may be formed on the continuous base carrier sheet 70, as shown in FIG. 5. The base carrier sheet 70 and the top carrier sheet 75 may later be cut, for instance along cut lines 118, in order to form separated absorbent cores. In at least some embodiments, a knife roll may be used to cut the base carrier sheet 70 and the top carrier sheet 75 into separated absorbent cores.

Figure 6A:
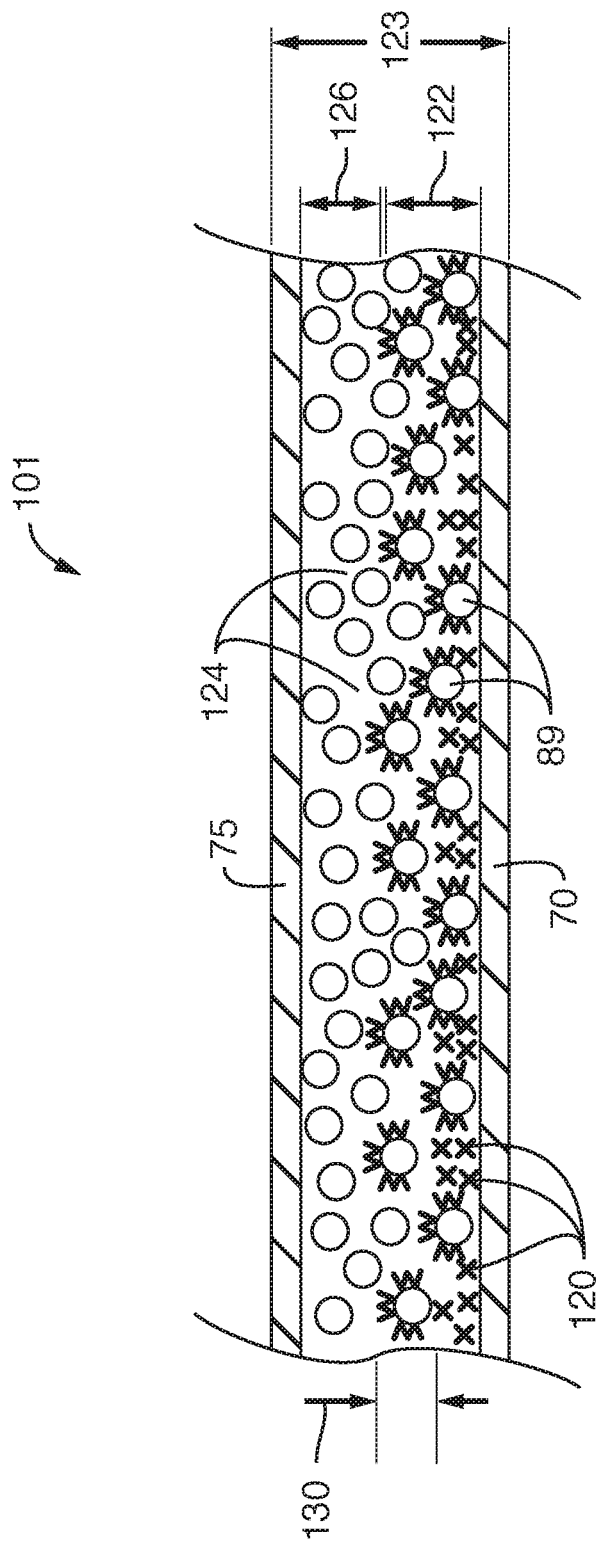
FIG. 6A is a cross-section view of an exemplary absorbent core that may be produced by the assembly of FIG. 1.

FIG. 6A depicts an example cross-section of an absorbent core 101 taken along line A-A' in FIG. 5. In the example of FIG. 6A, the absorbent core 101 was formed using only two adhesives. For instance, the absorbent core 101 of FIG. 6A includes the base carrier sheet 70. On top of the base carrier sheet 70 is the first adhesive 120, represented by the 'x's. The first adhesive 120, in some embodiments, may comprise and adhesive such as adhesive 78 described with respect to FIG. 1. Adhesive 120 may have been applied to the base carrier sheet 70, for instance, in the first adhesive application zone 80 of FIG. 1.

On top of the first adhesive 120 is the first amount of particulate material 122, represented by particulate material particles 89. The first amount of particulate material 122 may have been applied to the first adhesive 120, for example, in the particulate material delivery chamber 60a of FIG. 1. The first amount of particulate material 122 may have a thickness of between about 0.1 mm and about 1 mm.

On top of the first amount of particulate material 122 is the second adhesive 124, represented by the 'w's. The second adhesive 124, in some embodiments, may comprise an adhesive such as adhesive 88 described with respect to FIG. 1. The second adhesive 122 may have been applied to the first amount of particulate material 122, for instance, in the second adhesive application zone 81 of FIG. 1.

On top of the second adhesive 124 is the second amount of particulate material 126. The second amount of particulate material 126 may have been formed, for example, in the particulate material delivery chamber 60b of FIG. 1. The second amount of particulate material 126 may have a thickness of between about 0.1 mm and about 1 mm. Finally, the top carrier sheet 75 is shown disposed on top of the second amount of particulate material 126.

In some embodiments, some of the adhesive 124 may penetrate into the first amount of particulate material 122. For instance, in the example of FIG. 6A, strands of the first adhesive 124 (as represented by the 'w's) are shown penetrating the first amount particulate material 122 a distance 130. In some examples, distance 130 may range from between about 0.1 mm to about 1 mm. Generally, where the adhesive 124 is a SAAB adhesive, the distance 130 may be on the higher end of the range, as SAAB may be more effective at penetrating the first amount of particulate material 122 than other types of adhesives, such as hot-melt adhesive. The greater penetration distance of SAAB may allow for relatively greater stabilization of the particulate material 89 than other types of adhesive that have lesser penetrating ability.

Figure 6B:
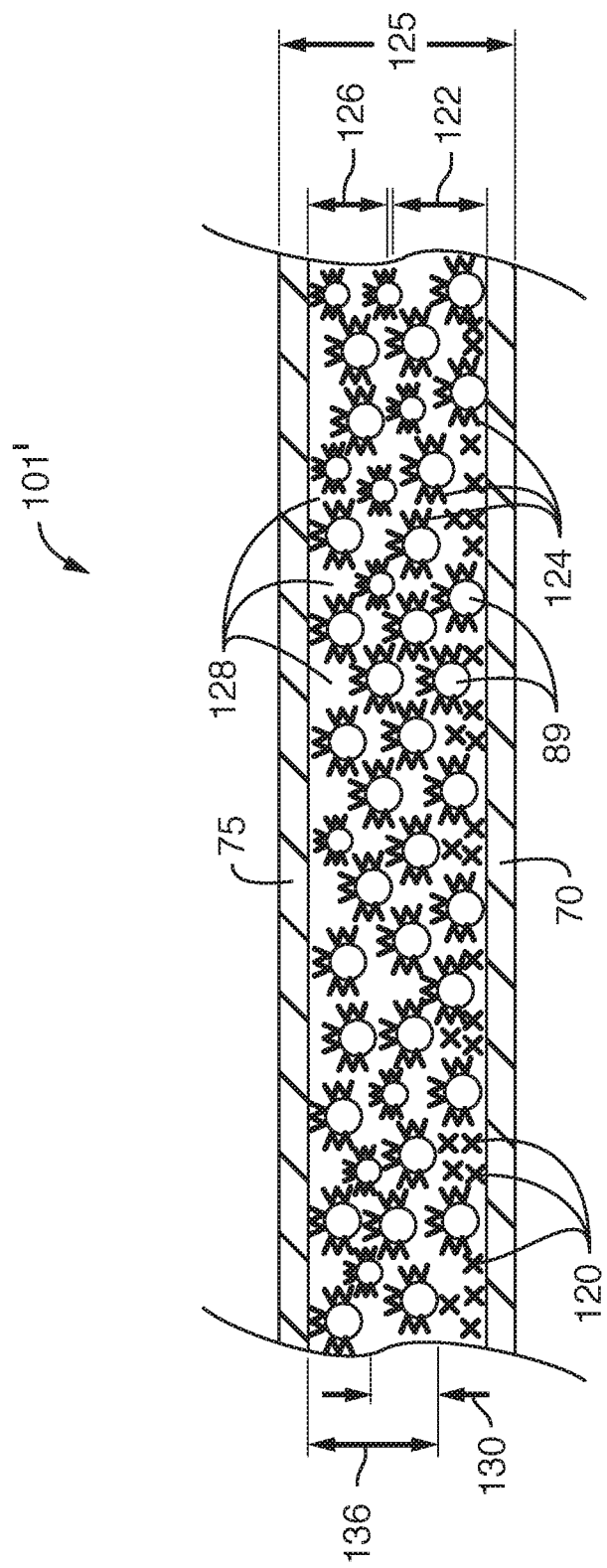
FIG. 6B is a cross-section view of an alternative exemplary absorbent core that may be produced by the assembly of FIG. 1.

FIG. 6B depicts an example cross-section of an alternative absorbent core 101' taken along line A-A' in FIG. 5. In the example of FIG. 6B, the absorbent core 101' was formed using three separate adhesive applications. For instance, the absorbent core 101' of FIG. 6B may be the same as the absorbent core 101 of FIG. 6A except that the absorbent core 101' of FIG. 6B further includes third adhesive 128, which is also represented by 'w's. This is because in the embodiment of FIG. 6B, the second adhesive 124 and the third adhesive 128 are the same adhesive, such as a SAAB adhesive, but may have been applied in separate process steps.

The third adhesive 128, in some embodiments, may comprise adhesive 98a of FIG. 1. In these examples, the third adhesive 128 may have been applied to the second amount of particulate material 126 in the third adhesive application zone 91a. As with the second adhesive 120, the third adhesive 128 may penetrate at least partially into the particulate material 89. The penetration distance of the third adhesive 120 is shown by penetration distance 136, which may range from about 0.1 mm to about 2 mm. In at least some embodiments, the third adhesive 128 may penetrate throughout the entire laminate structure of absorbent core 101'.

In other embodiments, however, the third adhesive 128 may not be the same as the second adhesive 124. For instance, in at least some contemplated embodiments, the third adhesive may be applied to the top carrier sheet 75 rather than the second amount of particulate material 126. In these embodiments, the third adhesive may be a hot-melt adhesive rather than a SAAB adhesive, as SAAB adhesives may not be suitable for application to carrier sheets. Accordingly, the third adhesive 128 may be applied to the top carrier sheet such as in third adhesive application zone 91b of FIG. 1 instead of in third adhesive zone 91a.

In general, as shown in FIGS. 6A and 6B, absorbent cores 101 and 101' may have overall thicknesses 123, 125, respectively. Some suitable values for thicknesses 123, 125 range from between about 0.2 mm to about 2.0 mm. However, as will be described in more detail with respect to FIG. 8, the processes described herein may further include additional applications of adhesive and of particulate material, forming even larger laminate structures.

In even further additional or alternative embodiments, one or more tissue or other non-woven sheets may be interspersed between the adhesives and particulate material of the absorbent cores 101, 101'. With specific respect to FIG. 6A, for instance, in some embodiments an intermediate tissue or other non-woven material (not shown) may be placed on top of the first amount of particulate material 122. Then, the second amount of particulate material 126 may be deposited onto that intermediate tissue or other non-woven material. In further embodiments, an adhesive may then be applied to the laminate structure, as shown in FIG. 6B. Although only shown with two separate application of particulate material, as will be described in more detail with respect to FIG. 8, contemplated absorbent cores may include any suitable number of applications of particulate material. Accordingly, in such embodiments, an intermediate tissue or other non-woven sheet may be disposed between each adjacent application of particulate material.

Figure 7:
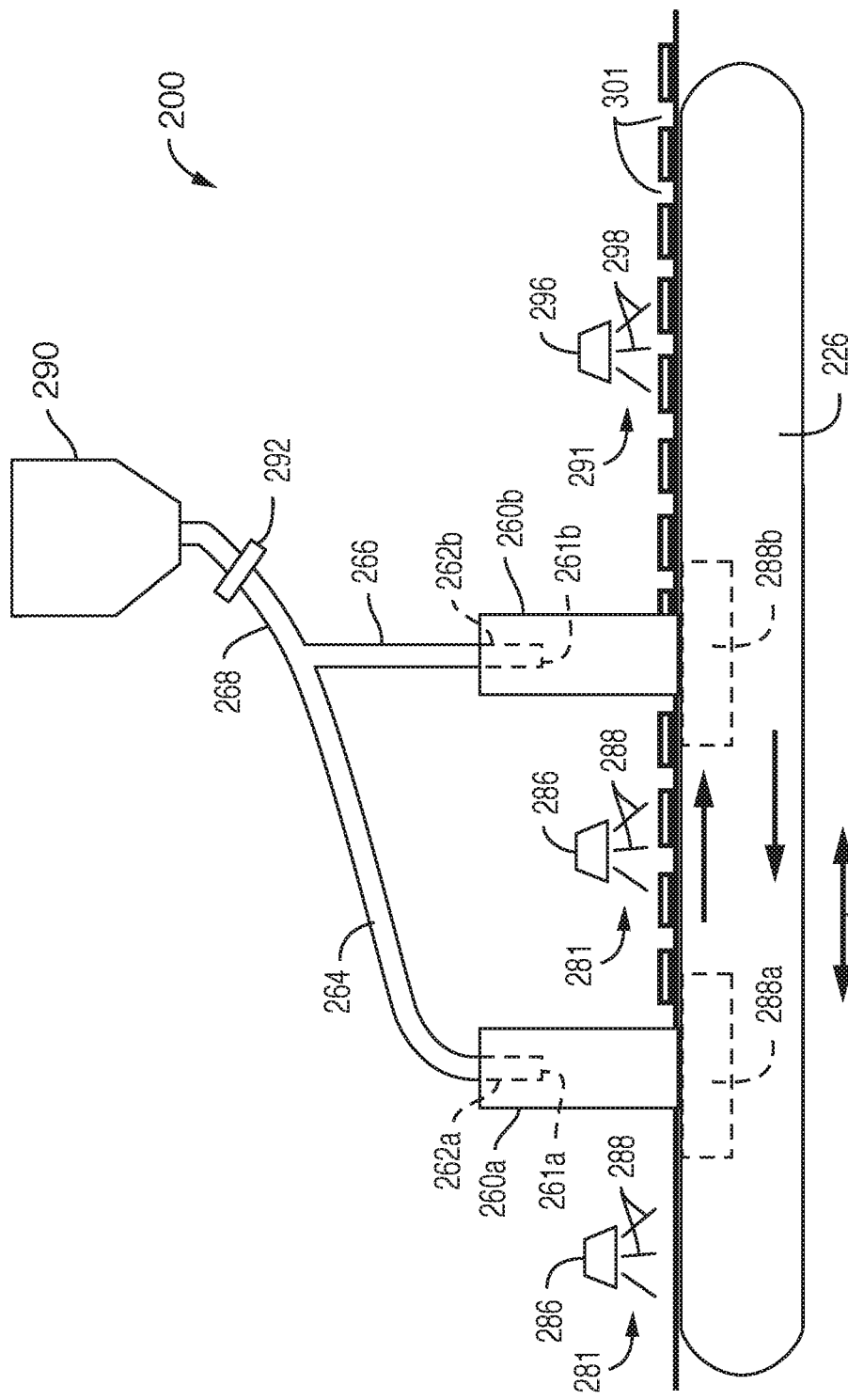
FIG. 7 is an alternative schematic of an example forming assembly for forming absorbent cores.

FIG. 7 depicts an alternative pulpless absorbent core forming apparatus 200. Pulpless absorbent core forming apparatus 200 may generally be similar to apparatus 20, except that instead of using a forming drum, pulpless absorbent core forming apparatus 200 uses a planer forming conveyer 226. Although the apparatus 200 may be slightly different from the apparatus 20, the method of forming pulpless absorbent cores with the apparatus 200 is very similar to the process described with respect to apparatus 20. For instance, the base carrier sheet 270 is first fed onto the forming conveyer 226. The base carrier sheet 270 then encounters adhesive application zone 281, where adhesive applicator 276 applies adhesive 278 to the base carrier sheet 270.

Next, the base carrier sheet 270 may enter particulate material delivery chamber 260a. Particulate material may be delivered to the particulate material delivery chamber 260a from the hopper 290 through connecting pipe 268 and delivery pipe 264. Delivery pipe 264 may enter the particulate material delivery chamber 260a and form particulate material delivery conduit 262a. The particulate material delivered to the particulate material delivery conduit 262a ultimately exits the particulate material delivery conduit 262a through inlet 261a. In some embodiments, a metering device 292 may be present to meter out a specific amount of particulate material from the hopper 290 to ensure a predetermined amount of particulate material flows to particulate material delivery conduit 262a.

Additionally, in at least some of these embodiments, a vacuum chamber 228a may be present under the forming conveyer. For instance, the forming conveyer may have a foraminous forming surface (not shown) and air may be able to move across the foraminous forming surface. In the region of vacuum chamber 228a, air may be moving from within the particulate material delivery chamber 260a through the foraminous forming surface and into a duct (not shown) coming out of the forming conveyer 226. This movement of air may pull particulate material exiting inlet 261a toward the forming conveyer to be deposited onto the adhesive 278 and the base carrier sheet 270 forming a layer comprising a first particulate material. Although vacuum ducts 228a and 228b are shown only in the vicinity of the particulate material delivery chambers 260a, 260b, in other embodiments, vacuum chambers 228a, 228b may extend outside of the region around the particulate material delivery chambers 260a, 260b and over a greater extent of the forming conveyer 226 than is shown in FIG. 7.

After exiting the particulate material delivery chamber 260a, the base carrier sheet 270, now including adhesive 278 and a first amount of particulate material, encounters adhesive application zone 281. Within adhesive application zone 281, an adhesive applicator 286 applies adhesive 288 onto the first amount of particulate material that was deposited onto adhesive 278 and the base carrier sheet 270 within the particulate material delivery chamber 260a.

The base carrier sheet 270 may then enter the particulate material delivery chamber 260b. Particulate material may be delivered to the particulate material delivery chamber 260b through connecting pipe 268 and through delivery pipe 266. Delivery pipe 266 may enter the particulate material delivery chamber 260b and form particulate material delivery conduit 262b, which in turn may end at inlet 261b. Particulate material delivered from the hopper 290 may exit inlet 261b and be drawn toward the adhesive 288 due to vacuum chamber 228b. Ultimately, a second amount of particulate material may be deposited onto the adhesive 288.

Further processing steps may be included to ultimately form pulpless absorbent cores 301. For instance, in some embodiments, a top carrier sheet (not shown) may be applied over the second amount of particulate material. Additionally, a third adhesive zone 291 may be included where adhesive applicator 296 applies a third adhesive, adhesive 298 onto the second amount of particulate material, or, alternatively, onto the top carrier sheet before the top carrier sheet is applied to the second amount of particulate material. In still further embodiments, the resulting pulpless absorbent cores may be further processed, for example by delivery through a nip roller, or separation by a knife roll. Generally, any of the additional or alternative process steps described with respect to apparatus 20 may also be implemented with respect to apparatus 200.

Figure 8:
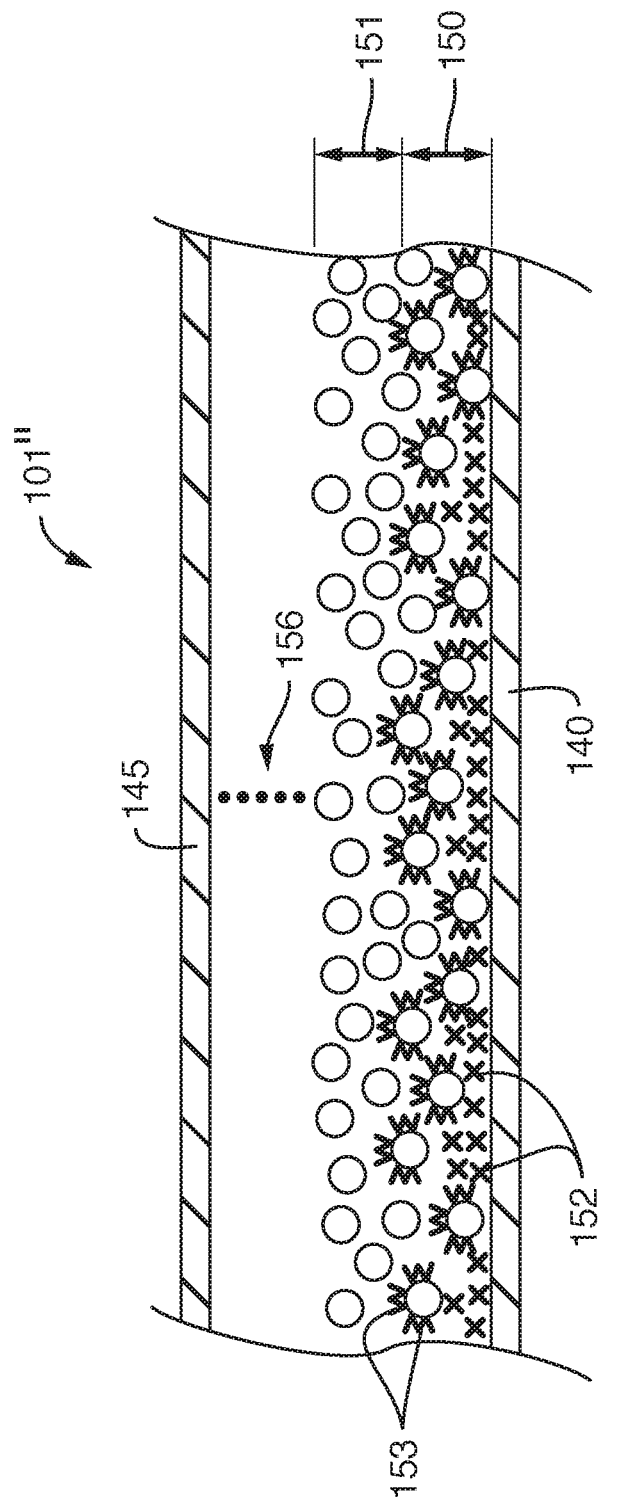
FIG. 8 is a cross-section view of an alternative exemplary absorbent core that may be produced by the assembly of FIG. 1 or FIG. 7.

In further alternative embodiments, it should be understood that the pulpless absorbent cores contemplated by this disclosure are not limited to only two particulate material applications. For instance, FIG. 8 depicts a generic pulpless absorbent core 101″ that may be formed according to the techniques disclosed herein and having any suitable number of particulate material applications. The pulpless absorbent core 101″ includes a base carrier sheet 140, a top carrier sheet 145, and a first amount of particulate material 150 and a second amount of particulate material 151. The pulpless absorbent core 101″ further includes a first adhesive 152 and a second adhesive 153. The adhesives 152, 153 and the first and second amounts of particulate material 150, 151 may be applied in a manner similar to that described with respect to apparatus 20 or 200.

However, pulpless absorbent core 101″ may be formed from any suitable number of additional adhesive and particulate material applications. For instance, each pair of an additional application of adhesive and another amount of particulate material may be thought as a unit building up the absorbent core 101″. Accordingly, apparatus 20 or 200 may be modified to include additional adhesive application zone and particulate material delivery chamber units situated after second adhesive application zone 81 and particulate material delivery chamber 60b or adhesive application zone 281 and particulate material delivery chamber 260b. For each additional adhesive application zone and particulate material delivery chamber unit, pulpless absorbent core 101″ may include another adhesive and amount of particulate material. Although the pulpless absorbent core 101″ is contemplated to include any number of suitable additional units of adhesive and particulate material, as indicated by dots 156, some example suitable number of adhesive and particulate material units include 3, 4, 5, 6, and 7.

Figure 9:
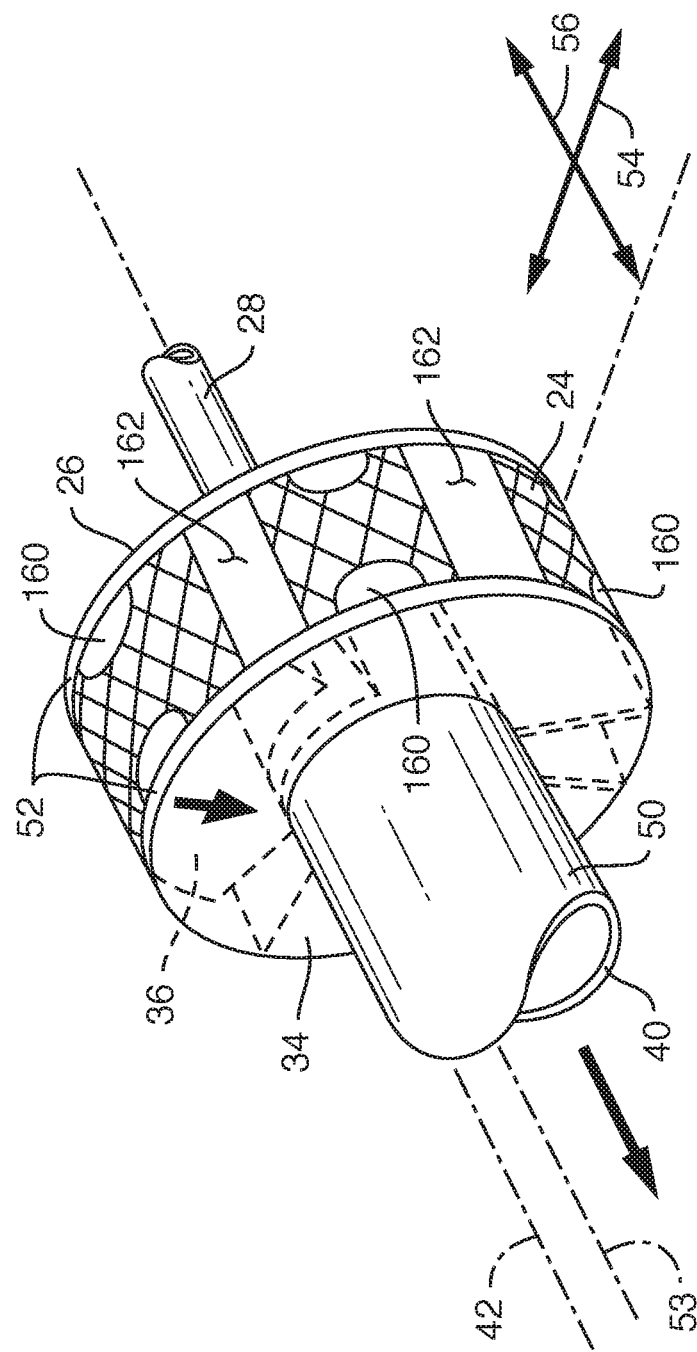
FIG. 9 is a perspective view of a forming drum including a plurality of masking members for forming shaped absorbent cores.

As mentioned previously, in some embodiments, one or more masking members may be used in order to form shaped pulpless absorbent cores. FIG. 9 depicts forming drum 26 including example masking members 160, although similar masking members may be used with forming conveyer 226. Masking members 160 mask portions of the forming surface 24, creating a pattern of shaped un-masked areas of the forming surface 24. These shaped un-masked areas will affect a distribution of particulate material within the resulting absorbent cores, thereby helping to create the shaped absorbent cores.

Figure 10:
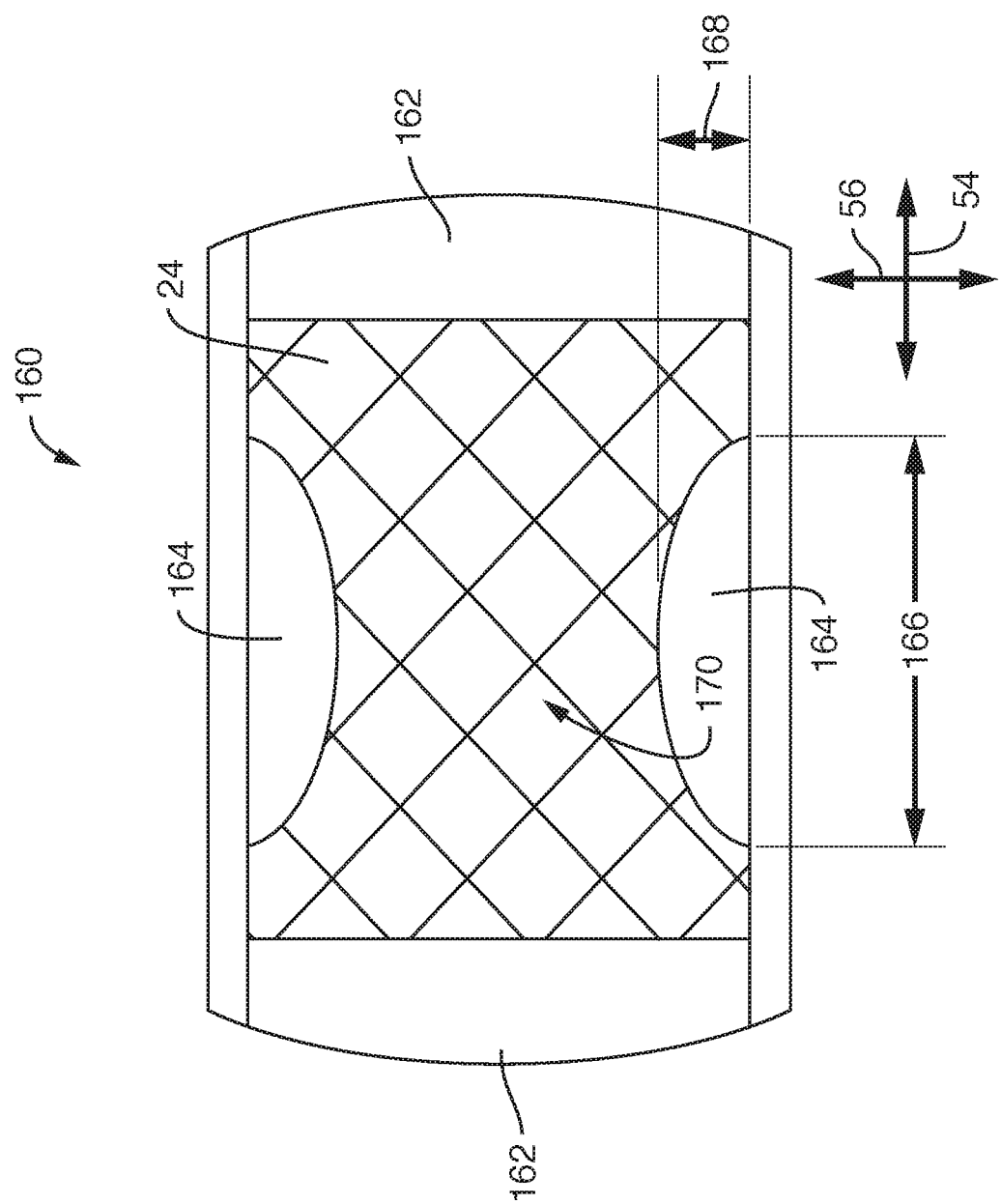
FIG. 10 is a top view of a masking member disposed on the forming drum of FIG. 9.

Although only shown with one example shape in FIGS. 9 and 10, in other suitable embodiments, the masking members 160 can have any number of different patterns. In still further embodiments, each of the masking members 160 can have different patterns and may be arranged in any order on the forming drum 26. The illustrated system of masking members 160 in FIG. 9 includes substantially identical masking members 160 arranged consecutively around the circumference of the forming drum 26. The masking members 160 can be joined and assembled to the forming drum 26 and/or the forming surface 24 by employing any conventional attaching or mounting mechanisms. For example, the masking members 160 may be secured to the forming surface 24 by a plurality of bolts inserted through holes in the masking members 160 and the forming surface 24.

The masking members 160 may have any shape suitable for mounting onto the forming surface 24. For example, the masking members 160 may have an outer perimeter that forms a substantially rectangular shape. Additionally, the masking members 160 may have a slight curve along their length in the machine direction 54 to form an arc for fitting on the cylindrical forming surface 24. In other suitable embodiments, the masking members 160 may be substantially flat for fitting on planar forming surfaces, such as the planer forming conveyer 226 of apparatus 200. The curve of each masking member 160 may have a radius substantially equal to the radius of the forming surface 24 such that the masking members 160 fit on the forming surface 24. When joined together, a series of masking members 160 can completely concentrically encircle the circumference of the forming surface 24.

FIG. 10 depicts a close-up of one exemplary masking member 160 disposed over the forming surface 24. As can be seen in FIG. 10, masking member 160 includes both masking end portions 162 and masking side portions 164. Masking side portions 164 may extend along the masking member 160 for a distance 166. Some example values of distance 166 may range from about 10 cm to about 30 cm. Additionally, masking side portions 164 may extend inward from the edges of the masking member 160 a distance 168. Some example values of distance 168 may range from about 1 cm to about 10 cm. The masking side portions 164 may act to form a crotch region 170 in the resulting formed absorbent cores.

When the masking members 160 are used within the processes described with respect to apparatus 20 and apparatus 200, the masking members 160 may affect a distribution of particulate material within a resulting absorbent core. As described previously, as the base carrier sheet travels around the forming drum 26, the base carrier sheet may be drawn to the forming surface 24 by the use of a vacuum drawing air through forming surface 24 and into an interior of the forming drum 26. Additionally, as the base carrier sheet travels through a particulate material delivery chamber, the particulate material may be drawn to the base carrier sheet by the vacuum. Where masking members 160 are used, the base carrier sheet travels around the forming drum 26 on top of the masking members 160, which effectively block air moving through the forming surface 24 in the masked areas. Accordingly, as the base carrier sheet travels through a particulate material delivery chamber, the particulate material will be drawn preferentially onto the base carrier sheet over the un-masked areas of the forming surface 24.

Figure 11:
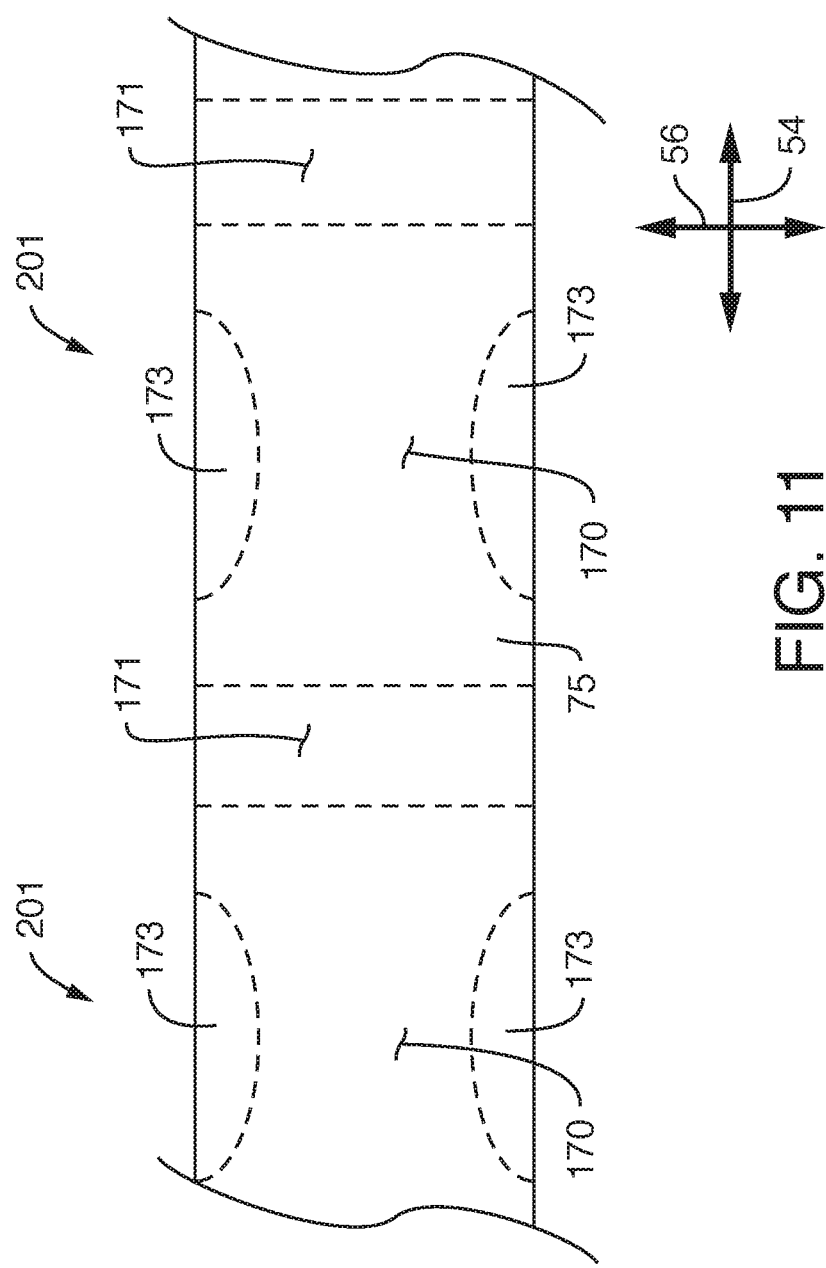
FIG. 11 is an illustration of an exemplary shaped absorbent core structure that may be produced using the forming drum and masking members of FIGS. 9 and 10.

FIG. 11 depicts example shaped absorbent cores 201 that may be formed using the masking members 160. In the example of FIG. 11, different regions of the shaped absorbent cores 201 are shown with dashed lines. The shaped absorbent cores 201 may include regions of relatively higher average basis weights, such as within the crotch regions 170 and other regions where the forming surface 24 was uncovered by the masking members 160. The shaped absorbent cores 201 may also include regions of relatively lower average basis weights, such as in end regions 171 and leg regions 173. In embodiments contemplated by this disclosure, the areas of relatively higher average basis weights may have average basis weights ranging from between about 100 grams per meter (gsm) to about 1000 gsm. The areas of relatively lower average basis weights may have average basis weights ranging from between about 0 gsm to about 100 gsm. In some embodiments, the shaped absorbent cores 201 may be separated into individual shaped absorbent cores by cutting the length of resulting shaped absorbent cores 201 in the end regions 171.

The shaped absorbent cores 201 formed using masking members, such as masking members 160, may have some benefits over non-shaped absorbent cores. For instance, the regions of lower basis weights may allow the shaped absorbent cores 201 to have a lower overall particulate material content than non-shaped cores, resulting in lower manufacturing costs. However, because of the locations of the areas of higher basis weights, overall absorption performance of the shaped absorbent cores 201 may be at least the same as corresponding non-shaped absorbent cores.

Figure 12:
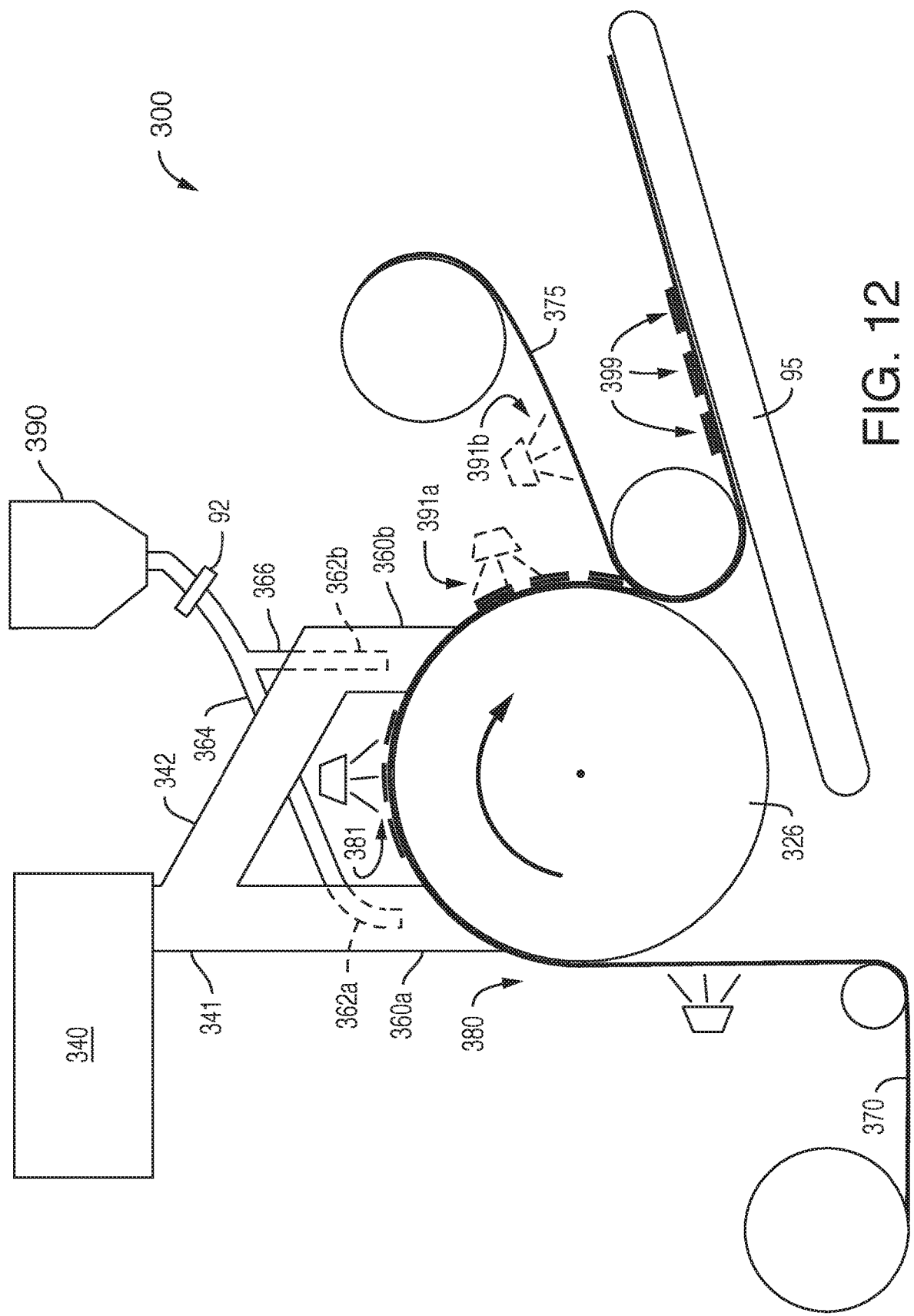
FIG. 12 is a schematic of an example forming assembly for forming absorbent cores including both pulp fluff and particulate absorbent material.

As mentioned previously, the pulpless absorbent cores of the present disclosure may be truly pulpless, or the pulpless absorbent cores may have a relatively small pulp content. For example, some of the pulpless absorbent cores of the present disclosure may include an amount of cellulose fibers that is between about 0.5% and about 10%, by weight, of the total contents of the cores. The addition of a small amount of cellulose fibers to the absorbent cores the present disclosure may impart a greater feeling of softness or provide other beneficial properties to the absorbent cores. FIG. 12 depicts one example apparatus, apparatus 300, which may be used to form the pulpless absorbent cores that have a small pulp content.

Apparatus 300 is very similar to apparatus 20 of FIG. 1. For instance, a base carrier sheet 370 may be fed onto forming drum 326. The base carrier sheet 370 may then advance through a series of adhesive applications zone 380, 381 (and, possibly 391a or 391b) and particulate material delivery chambers 360a, 360b. A top carrier sheet 375 may then be applied to form the resulting absorbent cores 399.

One difference between apparatus 20 and apparatus 300 is that apparatus 300 may further include fiberizer 340. In the embodiment of FIG. 12, the fiberizer 340 may be fed pulp or cellulose sheets and break up the cellulose sheets into many individual fibers. The fiberizer 340 may be a hammer mill-type fiberizer, or any other suitable type of fiberizer known in the art. The cellulose fibers may exit the fiberizer 340 into delivery ducts 341 and 342. The delivery ducts may ultimately form material delivery chambers 360a, 360b.

The material delivery chambers 360a, 360b may differ from the particulate material delivery chambers 60a, 60b of apparatus 20 in that the material delivery chambers 360a, 360b may deliver both particulate material and cellulose fibers to the base carrier sheet. For example, cellulose fibers may travel through the delivery ducts 341, 342 and enter the material delivery chambers 360a, 360b. Gravity, along with the vacuum pressure within the material delivery chambers 360a, 360b will cause the cellulose fibers to deposit onto the base carrier sheet 370.

Particulate material may also be delivered to the material delivery chambers 360a, 360b. For instance, particulate material may be stored in hopper 390 and may be delivered to the material delivery chambers 360a, 360b through delivery pipes 364, 366. The delivery pipes 364, 366 may ultimately form particulate material delivery conduits 362a, 362b within the material delivery chambers 360a, 360b. The delivered particulate material may exit the particulate material delivery conduits 362a, 362b within the material delivery chambers 360a, 360b. Similar to the pulp fibers, gravity and the vacuum pressure within the material delivery chambers 360a, 360b will cause the particulate material to be deposited onto the base carrier sheet 370. In this manner, apparatus 300 may be used to form pulpless absorbent cores containing an amount of cellulose fibers representing between about 0.5% and about 10% of the total weight of the materials within the pulpless absorbent cores.

Figure 13:
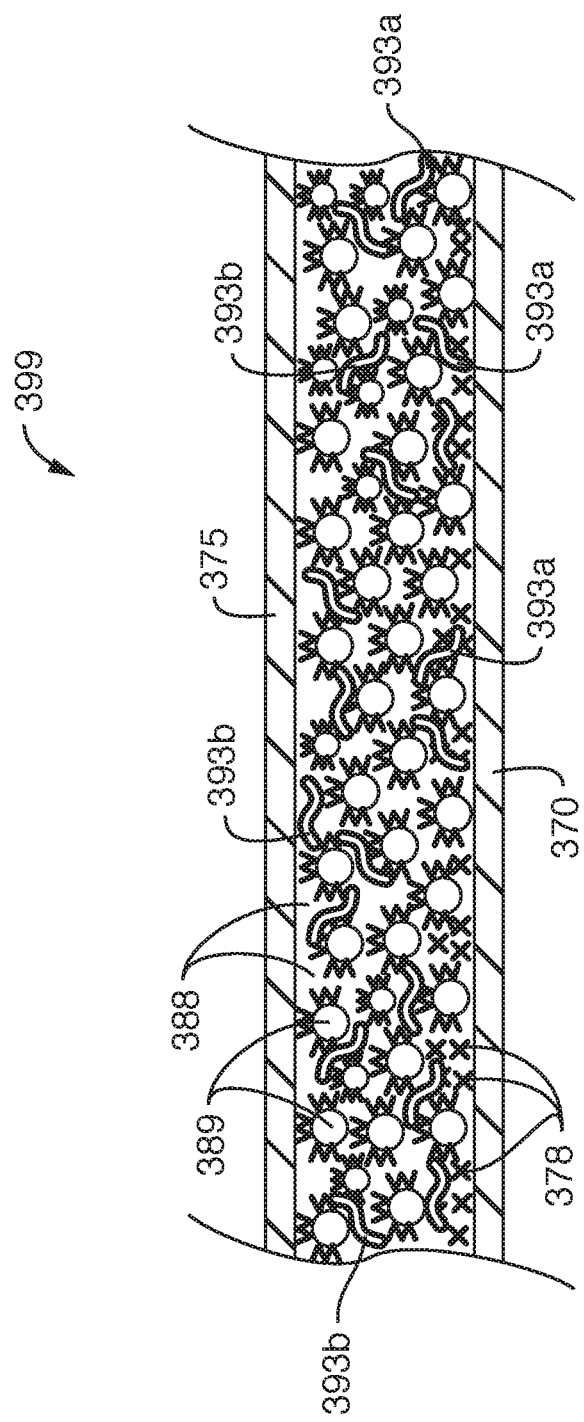
FIG. 13 depicts a cross-section of an exemplary absorbent core that may for formed by the forming assembly of FIG. 12.

FIG. 13 depicts a cross-section of an example absorbent core 399 that may be formed by the apparatus 300. FIG. 13 depicts absorbent core 399 including base carrier sheet 370 and top carrier sheet 375. Absorbent core 399 also includes adhesives 378 and 388, represented by 'x's and 'w's, respectively. In general, the absorbent core 399 may be similar to, and may be formed similarly to, the other absorbent cores of the present disclosure, such as absorbent cores 101, 101', and 101". Unlike the previous absorbent cores, however, absorbent core 399 further includes cellulose fibers 393a, 393b. As can be seen, cellulose fibers 393, 393b are disposed intermixed with the individual particulate material particles 389. Cellulose fibers 393a may be deposited, for instance, along with a first amount of particulate material particles 389, such as in particulate material delivery chamber 360a of FIG. 12. Cellulose fibers 393b may be deposited, for instance, along with a second amount of particulate material particles 389, such as in particulate material delivery chamber 360b of FIG. 12. As mentioned previously the addition of cellulose fibers may impart a greater softness to absorbent cores of the present disclosure, and the cellulose fibers may further help to stabilize the particulate material particles 389 between the base carrier sheet 370 and the top carrier sheet 375.

Again, it should be understood that FIG. 12 only represents one contemplated embodiment. In further embodiments, apparatuses 20 and/or 200 may be modified to include only a single particulate material delivery chamber that further intermixes cellulose fibers with the particulate material before deposition at a forming surface, instead of the two shown with respect to FIG. 12. In general, the apparatuses 20 and/or 200 may include a number of particulate material delivery chambers that allow for the intermixing of cellulose fibers and particulate material that is less than all of the particulate material delivery chambers of the apparatuses. In these alternative embodiments, then, a relatively smaller proportion of the formed absorbent cores may include cellulose fibers. For instance, if the cellulose fibers were intermixed with a first amount of particulate material, the mixture of cellulose fibers and particulate material may be located proximate the base carrier sheet. However, if the cellulose fibers were intermixed with a second (or third, fourth, etc.) amount of particulate material, the mixture of cellulose fibers and particulate material may be located closer to the top carrier sheet than the first amount of particulate material.

Figure 14A:
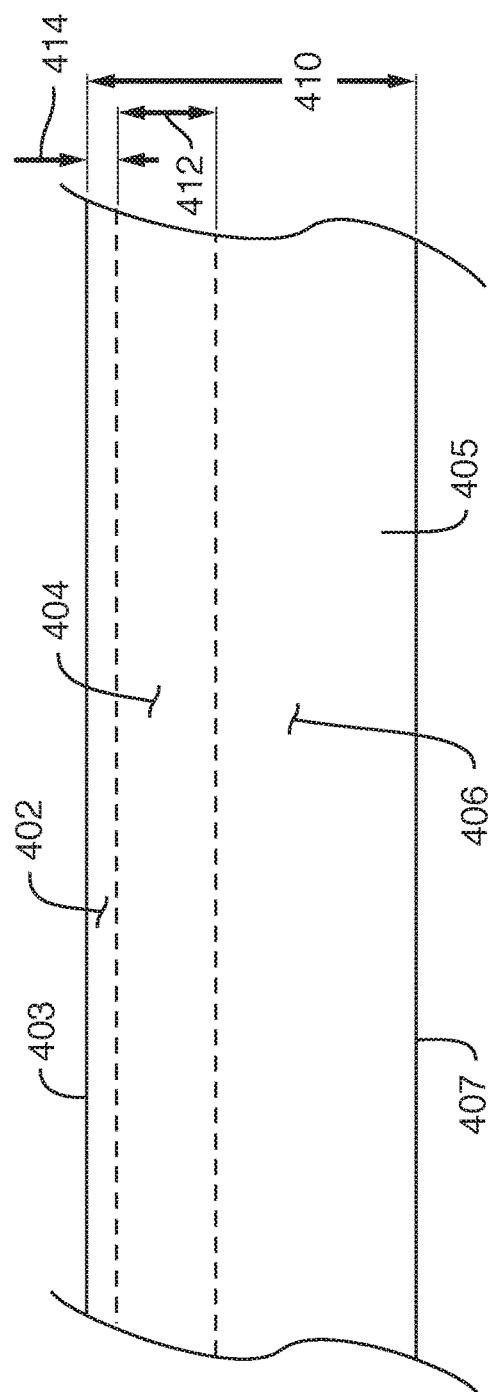
FIGS. 14A and 14B are illustrations of carrier sheets that may be used to form absorbent cores.
Figure 14B:
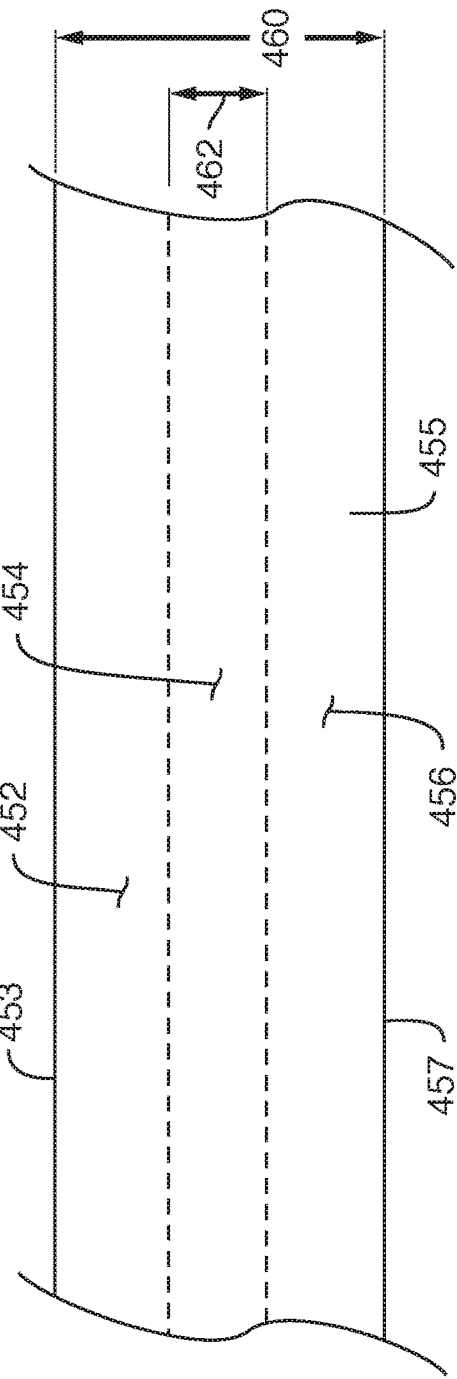

In alternative embodiments, instead of forming the pulpless absorbent cores of the present disclosure with both a base carrier sheet and a top carrier sheet, as described previously, some contemplated methods may only use a single carrier sheet. FIGS. 14A and 14B depict example embodiments where a single carrier sheet may be used instead of both a base carrier sheet and a top carrier sheet.

FIG. 14A depicts carrier sheet 405. In some embodiments, carrier sheet 405 may have a first edge region 402 having a first edge 403 and a second edge region 406 having a second edge 407, with a middle region 404 disposed between the first edge region 402 and the second edge region 406. In the embodiment of FIG. 14A, particulate material and adhesive may only be applied within the middle region 404. After application of adhesive and particulate material, instead of applying a second carrier sheet as described herein previously, the second edge region 406 may be folded over the middle region 404 and onto the first edge region 402 such that the second edge 407 is disposed proximate the first edge 403. The edges 403, 407 may then be bonded together to create an enclosed pulpless absorbent core. Bonding the edges 403 and 407 together may be done by any suitable method, such as by pressure bonding, adhesive bonding, ultrasonic bonding, or the like. The apparatuses described herein may be modified to produce such pulpless absorbent cores. For instance, instead of machinery to apply the top carrier sheets, the apparatuses described herein may include folding and bonding machinery, which are well known in the art, to fold the second edge region 406 onto the first edge region 402 and to bond the regions 402, 406 together.

In some embodiments according to FIG. 14A, the carrier sheet 405 may have a width 410. Width 410 may be greater than twice the width of a forming surface used to create pulpless absorbent cores, or alternatively greater than twice the width of an un-masked portion of a forming surface used to create pulpless absorbent cores. In some specific examples, width 410 may range between about 25 cm and about 60 cm.

The middle region 404 may have a width 412. The width 412 may range from between about 40% to about 50% of the overall width 410 of the carrier sheet 405. Additionally, the first edge region 402 may have a width 414 that is be between about 0.5% and about 10% of the overall width 410 of the carrier sheet 405.

FIG. 14B depicts another example embodiment of a single carrier sheet that may be used to form the pulpless absorbent cores of the present disclosure. In the example of FIG. 14B, the carrier sheet 450 may have an overall width 460. The overall width 460 may have values similar to those described with respect to width 410. Additionally, the carrier sheet 450 may have a first edge region 452, a middle region 454, and a second edge region 456. As with the embodiment of FIG. 14A, adhesive and particulate material may only be applied to the carrier sheet 450 within the middle region 454. After application of adhesive and particulate material to the middle region 454, one of the first edge region 452 or the second edge region 456 may be folded over onto the middle region 454. Then, the other of the first edge region 452 or the second edge region 456 may be folded over the middle region 454. In some embodiments, the edge regions 452, 456 may overlap over the middle region 454, and at least a portion of each of the first edge region 452 and the second edge region 456 may be bonded together to form an enclosed pulpless absorbent core.

Similarly to carrier sheet 405, in some embodiments the width 460 of the carrier sheet 450 may be greater than twice the width of a forming surface used to create pulpless absorbent cores, or greater than an un-masked portion of a forming surface used to create pulpless absorbent cores. However, this is not necessary in all embodiments. In at least some embodiments, width 460 may range between about 25 cm and about 60 cm.

The region 454 of the carrier sheet 450 may have a width 462. The width 462 may range from between about 33% to about 50% of the overall width 460 of the carrier sheet 450. In some embodiments, each of the first edge region 452 and the second edge region 456 may have a width (not shown) that is between about 25% and about 33% of the overall width 460. However, the widths of the first edge region 452 and the second edge region 456 do not necessarily need to be equal. For example, the width of the first edge region 452 may be between about 35% and about 40% of the overall width 460 and the width of the second edge region 456 may be between about 10% and about 25% of the overall width of 460, or vice versa.

Figure 15:
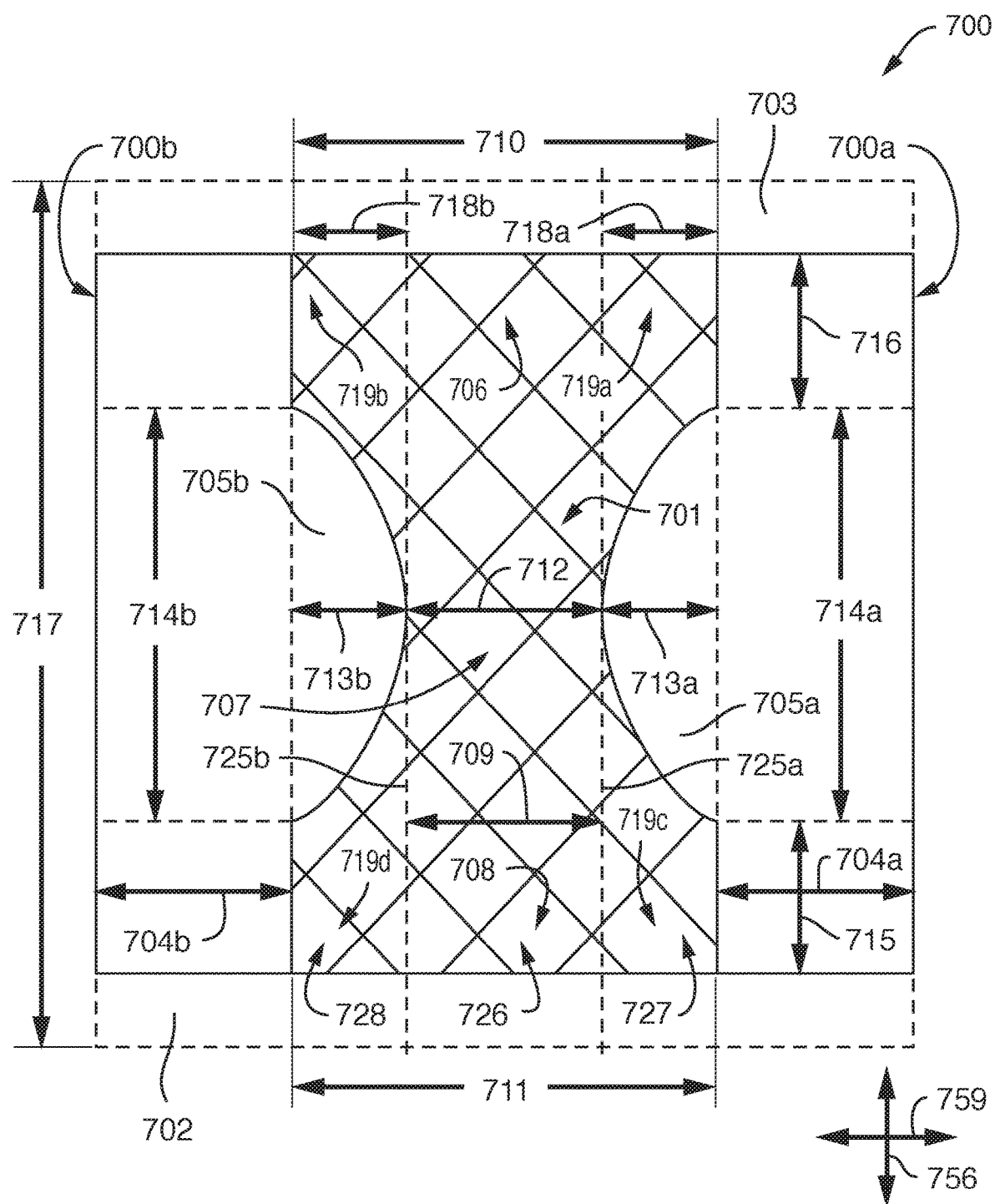
FIG. 15 is a plan view of an exemplary masking member defining an absorbent core region, according to aspects of the present disclosure.

FIG. 15 depicts exemplary masking member 700 that may be used in conjunction with any of the above described processes to produce absorbent cores. For example, masking member 700 may be similar to masking member 160 of FIG. 10, and may be used in a similar manner to masking member 160. Multiple masking members 700 may be attached to a forming drum or conveyer system, such as those described with respect to apparatuses 20 and 200, to mask portions of a foraminous forming surface. The multiple masking members 700 may be attached end to end to allow formation of a continuous length of absorbent cores. In some further embodiments, masking member 700 may comprise opposing masking portions 700a and 700b. Although, in some embodiments, masking member 700 may further comprise masking portions 702 and/or 703 depicted by dashed lines in FIG. 15, disposed at either ends of masking member 700 to form some separation between adjacent masking members 700.

Generally, when masking member 700 is disposed over a foraminous forming surface, masking member 700, which is made from a non-foraminous material, may block portions of the foraminous forming surface, thereby defining an absorbent core region on the forming surface. The absorbent core region may then be the un-masked foraminous portions of the foraminous forming surface. An exemplary absorbent core region shape 701 is depicted in FIG. 15 by a hatching pattern. In some embodiments, the absorbent core region 701 may comprise a rear core region 706 and a front core region 708. In these embodiments, each of the rear core region 706 and the front core region 708 may span half of overall length 717 of the absorbent core region 701.

In other embodiments, the absorbent core region 701 may additionally comprise crotch region 707. In some of these embodiments, each of the rear core region, the crotch region, and the front core region may span a third of overall length 717 of the absorbent core 701. Some example suitable values for the overall length 717 of the absorbent core region 701 range between about 10 cm and about 50 cm. In other of these embodiments, rather than be defined as a middle third of the absorbent core region 701, the crotch region 707 may be defined as the region bounded by shaped regions 705*a*, 705*b*. For instance, in the example of FIG. 15, the crotch region 707 may span a length 714*a* or 714*b* in the machine direction 754, which correspond to a length of the shaped regions 705*a*, 705*b* within the absorbent core region 701. Example values for lengths 714*a* and 714*b*, defining a length of shaped regions 705*a* may range between about 10 cm and about 30 cm. Additionally, shaped regions 705*a*, 705*b* may extend inward from the greatest cross-machine direction widths 710, 711 for a width 713*a*, 713*b*. Example suitable values for widths 713*a*, 713*b* may range between about 1 cm and about 10 cm. This may put a smallest cross-machine direction width 712 of the crotch region 707 between about 5 cm and about 25 cm. Accordingly, widths 713*a*, 713*b* may have values that are between about 5% and about 40% of the greatest cross-machine direction widths 710, 711.

Further, as shown in FIG. 15, the shaped regions 705*a*, 705*b* may have an arcuate shape. However, this is only an example. Generally, the shaped regions 705*a*, 705*b* may have any suitable shape. For instance, the shaped regions 705*a*, 705*b* may have any suitable shape where the area of the shaped regions 705*a*, 705*b* ranges between about 25% and about 50% of an area defined by the greatest cross-machine direction width 710 or 711, and the overall length 717.

The absorbent core region 701 may be divided up into a number of different regions running a length of the absorbent core region 701. One such region may include central region 726 having a width 709 running in the cross-machine direction 756, shown as extending between dashed lines 725*a*, 725*b* in FIG. 15. In some embodiments, the central region width 709 may be coextensive with the smallest cross-machine direction width 712. However, in other embodiments, the central region width 709 may be smaller or greater than the smallest cross-machine direction width 712. The absorbent core region 701 may further include a first edge region 727 having a first edge region width 718*a* and a second edge region 728 having a second edge region width 718*b*. The absorbent core region 701 may further include rear ear regions 719*a*, 719*b* and front ear regions 719*cb*, 719*d*. The rear ear regions 719*a*, 719*b* may be defined as regions above the shaped portions 705*a*, 705*b* and outside of the central region 726. Likewise, the front ear regions 719*c*, 719*d* may be defined as regions below the shaped portions 705*a*, 706*b* and outside of the central region 726.

Where masking member 701 includes shaped portions 705*a*, 705*b* defining the crotch region 707, the lengths of the rear core region 706 and the front core region 708, then, may be defined by lengths 716 and 715, respectively. Some exemplary values for lengths 716 and 715 may range between about 1 cm and about 15 cm for length 716 and between about 1 cm and about 15 cm for length 715. Each of the rear core region 706 and the front core region 708 may additionally extend in a cross-machine direction identified by widths 710 and 711, respectively. Although generally shown as rectangular, the rear core region 706 and front core region may curved or have any suitable shape. In these cases, then, widths 710 and 711 may represent the greatest cross-machine width of each of the rear core region 706 and the front core region 708. Example suitable values for widths 710 and 711 may range from between about 7 cm and about 30 cm.

In some embodiments, masking portions 700*a* and 700*b* may have widths 704*a*, 704*b*. In some embodiments, widths 704*a*, 704*b* may be coextensive with a width of the drum rim where masking member 700 is attached to a forming drum so as to not block the foraminous forming surface except in the areas of the shaped portions 705*a*, 705*b*. However, in other embodiments, widths 704*a*, 704*b* may be large enough to extend beyond the drum rim and over at portion of the foraminous forming surface.

Generally, masking members such as masking members 700 may be used to form absorbent cores having differing average basis weights within different regions of the absorbent cores. For instance, the masking members 700 may block airflow through the foraminous forming surface. This blocking of airflow may cause the particulate material exiting a particulate material delivery conduit to deposit onto the foraminous forming surface at different rates. This process is described in more detail below with respect to FIGS. 16A and 16B.

Figure 16A:
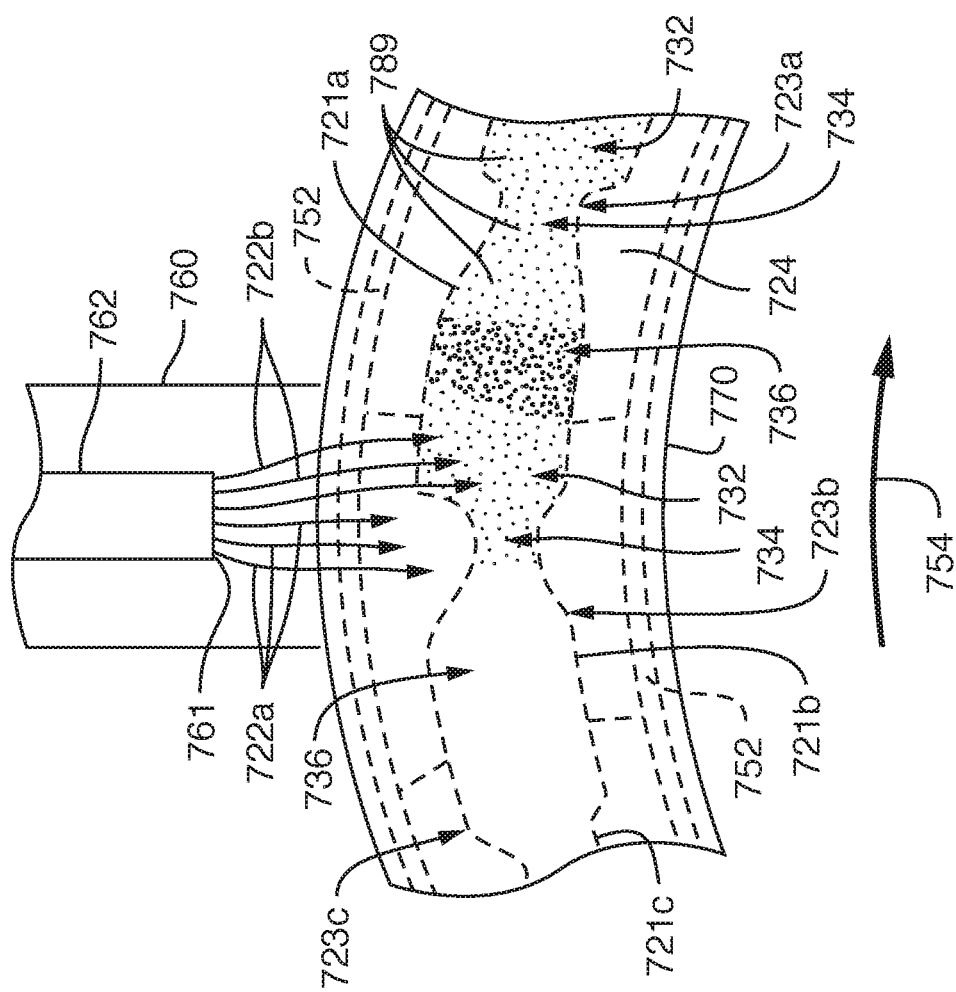
FIG. 16A is an internal view of an exemplary particulate absorbent material delivery conduit including particulate absorbent material depositing onto absorbent core regions of a carrier sheet.

FIG. 16A depicts a perspective view internal to exemplary particulate material delivery chamber 760. As can be seen, particulate material delivery chamber 760 includes particulate material delivery conduit 762 terminating with inlet 761. Additionally, foraminous forming surface 724 is shown disposed between drum rims 752 and under base carrier sheet 770. Foraminous forming surface 724 is also shown as including absorbent core regions 721*a-c*. The absorbent core regions 721*a-c* may be defined, for instance, by non-foraminous masking members, such as masking member 700 described with respect to FIG. 15.

The base carrier sheet 770 is shown disposed over the foraminous forming surface 724 and over the absorbent core regions 721*a-c*. The regions of the base carrier sheet 770 disposed over the absorbent core regions 721*a-c* may form base carrier sheet absorbent core regions 723*a-c*. Each of the base carrier sheet absorbent core regions 723*a-c* may be split into a base carrier sheet rear core region 732 and a base carrier sheet front core region 736, which may correspond to the underlying front core region and rear core region of a respective absorbent core region 721*a-c*. In examples where the absorbent core regions 721*a-c* further include a crotch region, the base carrier sheet absorbent core regions 723*a-c* may also further include a base carrier sheet crotch region 734 disposed between the base carrier sheet rear core region 732 and the base carrier sheet front core region 736. As can be seen in FIG. 16A, the base carrier sheet front core region 736 trails the base carrier sheet rear core region 732 in the machine direction 754.

FIG. 16A also depicts particulate material being deposited onto the base carrier sheet 770. For instance, FIG. 16A depicts individual particulate material 789 located within the base carrier sheet absorbent core region 723*a* and within a portion of the base carrier sheet absorbent core region 723*b*. Arrows 722*a* and 722*b* depict paths that particulate material 789 may follow upon exiting inlet 761 before depositing onto the base carrier sheet 770.

As the forming drum carrying the forming surface 724 and the one or more masking members underlying the base carrier sheet 770 moves in the machine direction, different portions of the forming surface 724 will pass under the particulate material delivery conduit 762. In embodiments where the underlying masking member or members include shaped regions, such as shaped regions 705a, 705b described with respect to masking member 700, a varying amount of un-masked surface area of the forming surface 724 will pass under the inlet 761.

In these embodiments, where relatively smaller un-masked areas of the forming surface 724 and relatively greater un-masked areas of the forming surface 724 pass under the inlet 761, the vacuum pulling air and the particulate material toward the forming surface 724 may affect an amount of the particulate material 789 deposited onto the base carrier sheet 770. For example, as the relatively smaller un-masked areas of the forming surface 724, such as the base carrier sheet crotch regions 724, traverse under the inlet 761, the shaped regions may block airflow through a portion of the forming surface 724. This airflow blocking alters how the falling particulate material deposits onto the base carrier sheet 760. As can be seen in FIG. 16A, where the narrower regions of the absorbent core region 723b pass under the inlet 761, the particulate material 789 may follow paths 722a which represent paths where the particulate material 789 falls and/or is pulled, toward the forming surface 724 at a relatively slower velocity. Where the wider regions of the absorbent core region 723b pass under the inlet 761, the particulate material 789 may follow paths 722b, which represent paths where the particulate material 789 falls and/or is pulled, toward the forming surface 724 at a relatively faster velocity. These distinctions in the velocity at which the particulate material 789 falls and/or is pulled, toward the forming surface 724 may be particularly distinct when introducing the particulate material 789 into the chamber 760 at relatively low velocities, such as the velocities described previously with respect to the processes 20, 200, and the other disclosed processes.

As the base carrier sheet 770 continues in the machine direction 754, as can be seen in FIG. 16B, the particulate material 789 that followed the paths 722a, rather than being deposited within the base carrier sheet crotch region 734 on top of the masked areas is instead deposited within either the base carrier sheet front core region 736 of the base carrier sheet absorbent core region 723b or within the un-masked areas of the crotch region 724. Additionally, as the relatively greater un-masked area of the forming surface 724 of the base carrier sheet front core region 736 passes under the inlet 761 in FIG. 16B, particulate material 789 exiting the inlet 761 falls and/or is pulled toward the forming surface 724 in both the base carrier sheet front core region 736 of the base carrier sheet absorbent core region 723b and the base carrier sheet rear core region 732 of the base carrier sheet absorbent core region 723c.

Ultimately, this shifting of the falling particulate material 789 may cause the base carrier sheet front core region 736 of the base carrier sheet absorbent core region 723b to have a higher average basis weight than the base carrier sheet rear core region 732 of the base carrier sheet absorbent core region 723c. Additionally, in at least some embodiments, the base carrier sheet crotch region 734 may have a higher average basis weight than the base carrier sheet rear core region 732. Further details about the relative basis weights of the different regions of the absorbent cores produced by the disclosed processes are discussed in more detail with respect to the following figures.

Figure 17:
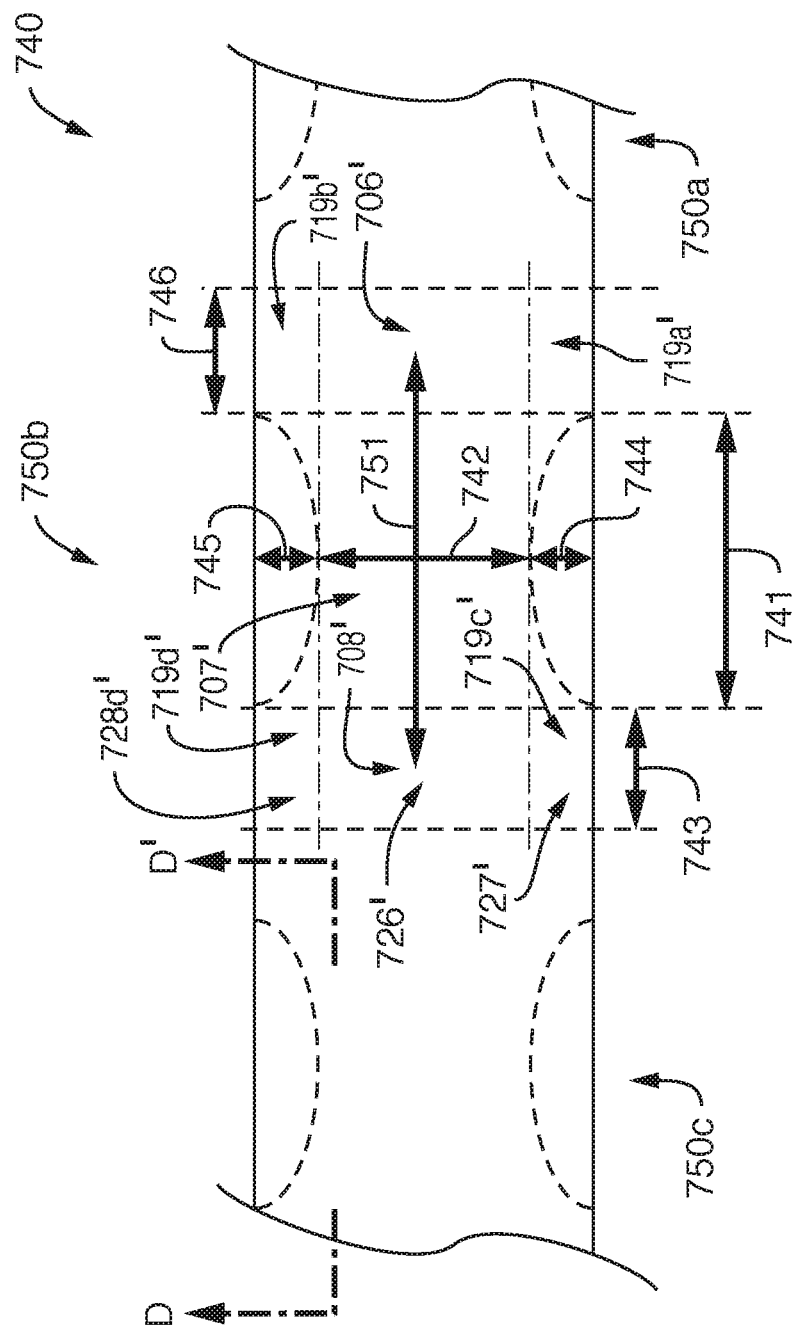
FIG. 17 is an illustration of exemplary absorbent cores that may be produced according to aspects of the present disclosure.

FIG. 17 depicts a strip of connected absorbent cores 740 that may be formed using any of the processes described herein and including one or more masking members as described with respect to FIG. 15. The strip of connected absorbent cores 740 shown in FIG. 17 include individual, connected absorbent cores 750a-c. At a later process step, the individual, connected absorbent cores 750a-c may be separated to form individual, separated absorbent cores for use in absorbent articles.

FIG. 17 also shows absorbent core 750b broken down into different regions. For instance, absorbent core 750b depicts rear core region 706', crotch region 707', and front core region 708'. FIG. 17 further depicts central region 726', first edge region 727', and second edge region 728'. FIG. 17 additionally includes rear ear regions 719a', 719b' and front ear regions 719c', 719d'. Dimensions including crotch region length 741, rear core region length 746, front core region length 743, first shaped region width 744, second shaped region width 745, and crotch region width 742 are all also shown in FIG. 17. These regions and dimensions may generally align with the similar regions and dimensions defined with respect to the absorbent core region 701 of FIG. 15. For instance, the dimensions of the regions in FIG. 17 may be equal to or similar to the dimensions of the similarly labeled regions in FIG. 15.

In some embodiments, using one or more masking members such as those described with respect to FIG. 15 along with any of the processes described herein may create zones of differing average basis weights within absorbent cores, such as absorbent core 750b. For example, the front core region 708' may have a higher average basis weight than the rear core region 706' and/or the rear ear regions 719a', 719b'. In some embodiments, the front core region 708' may have an average basis weight that is between 110% and 150% greater than the average basis weight of the rear core region 706' and/or the rear ear regions 719a', 719b'. In general, the average basis weight of the front core region 708' may range between about 200 gsm and about 800 gsm, while the average basis weight of the rear core region 706' and/or the rear ear regions 719a', 719b' may range between about 100 gsm and about 600 gsm.

Likewise, the front ear regions front ear regions 719c', 719d' may also have a higher average basis weight than the rear core region 706' and/or the rear ear regions 719a', 719b'. For instance, the front ear regions front ear regions 719c', 719d' may have an average basis weight that is between 110% and 150% greater than the average basis weight of the rear core region 706' and/or the rear ear regions 719a', 719b'. The average basis weight of the front ear regions front ear regions 719c', 719d' may also range between about 200 gsm and about 800 gsm.

In at least some further embodiments, the crotch region 707' may additionally have a higher average basis weight than the rear core region 706' and/or the rear ear regions 719a', 719b'. In some examples, the crotch region 707' may have an average basis weight that is between 110% and 150% greater than the average basis weight of the rear core region 706' and/or the rear ear regions 719a', 719b', similar to the front core region 708' with respect to the rear core region 706' and/or the rear ear regions 719a', 719b'. Although, in other embodiments, the crotch region 707' may have an average basis weight that is somewhat lower than the average basis weight of the front core region 708'. For example, the crotch region 707' may have an average basis weight that is between 105% and 125% greater than the average basis weight of either the rear core region 706' and/or the rear ear regions 719a', 719b'. Accordingly, in some examples, the crotch region 707' may have an average basis weight of between about 200 gsm and about 800 gsm, while in other examples, the crotch region 707' may have average basis weight that ranges between about 100 gsm and about 600 gsm.

Accordingly, as can be seen, the average basis weight of the absorbent core 750b may generally increase from the rear core region 706' to the front core region 708'. In some embodiments, the average basis weight of the absorbent core 750b may increase along a path between the rear core region 706' and the front core region 708', such as along path 751. In some specific embodiments, the average basis weight of the absorbent core 750b may increase linearly along path 751. However, in other embodiments, average basis weight of the absorbent core 750b may not increase in such a structured manner along path 751.

Using another metric, the total amount of particulate material within the different portions of the absorbent cores 750a-c may also differ. For instance, using absorbent core 750b as an example, greater than 60% of the total particulate material content of the absorbent core 705b may be located within a front half of the absorbent core 750b. The absorbent core 750b may have an overall length that is equal to the sum of the front core region length 743, the crotch region length 741, and the rear core region length 746. This total may equal the overall length 717 of the absorbent core region 701 described in FIG. 15. The front half of the absorbent core 750b, then, may be the portion of the absorbent core 750b spanning half of the sum of the front core region length 743, the crotch region length 741, and the rear core region length 746 that entirely overlaps the front core region 708'. The rear half of the absorbent core 705b, then, may be the portion of the absorbent core 750b spanning half of the sum of the front core region length 743, the crotch region length 741, and the rear core region length 746 that entirely overlaps the rear core region 706'. In further embodiments, greater than 70% of the total particulate material content of the absorbent core 750b may be located within the front half of the absorbent core 750b.

Additionally, the exemplary absorbent core 750b may be broken up into thirds. For instance, the absorbent core 750b may have a front third portion overlapping the front core region 708', a middle third portion overlapping the crotch region 707', and a rear third portion overlapping the rear core portion 706'. Each of these portions may span a third of an overall length of the absorbent core 750b, e.g. a third of the sum of the front core region length 743, the crotch region length 741, and the rear core region length 746, then the rear core region 706'. Using these thirds, the disclosed masking member and processes may cause the rear third portion to have an average basis weight that is between about 50% and about 90% of the average basis weight of the front third portion. In at least some additional embodiments, then the rear third portion may have an average basis weight that is between about 50% and about 90% of the average basis weight of the middle third portion. In some embodiments, greater than 40%, by weight, of the total particulate material content of the absorbent core 750b may be located within the front third portion.

Figure 18:
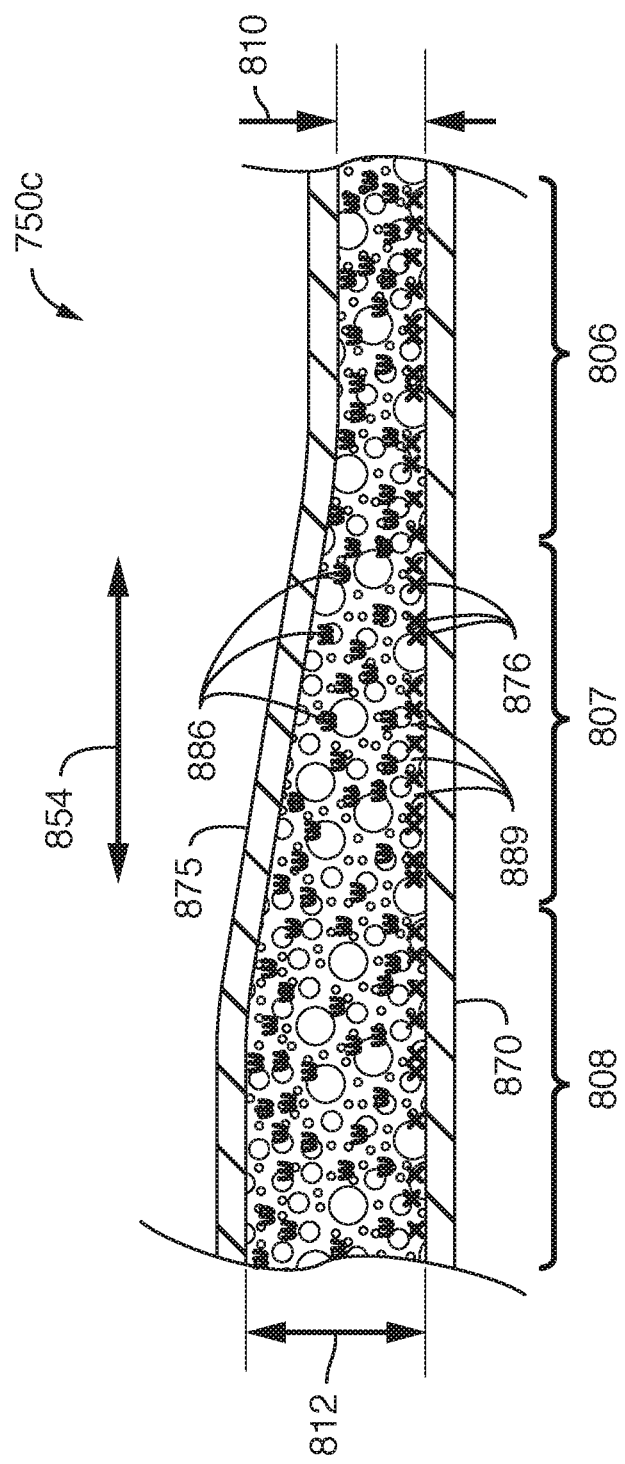
FIG. 18 is a cross-section view of an exemplary absorbent core taken along line D-D' of FIG. 17.

FIG. 18 depicts a cross-section view of the absorbent core 750c taken along line D-D'. As can be seen in FIG. 18, the absorbent core 750c comprises both a base carrier sheet 870 and a top carrier sheet 875. The absorbent core 750c further includes particulate material 889 stabilized with both a first adhesive 876 and a second adhesive 886. The first adhesive 876 may comprise a hot-melt adhesive, such as any of those described in this disclosure. The second adhesive 886 may comprise either a hot-melt adhesive or a SAAB adhesive, such as any of those described in this disclosure. The first adhesive 876 and the second adhesive 886 may act to maintain the positioning of the particulate material 889 within the absorbent core 750c.

The absorbent core 750c of FIG. 18 can be seen broken up into a rear core region 806, a crotch region 807, and a front core region 808, which span the absorbent core 750c in the machine direction 854. Additionally, as can be seen, each of the different regions 806, 807, and 808 have different average basis weights. For instance, near the rear core region 806, the absorbent core 750c has a particulate material depth 810, while the front core region 808 has a particulate material depth 812, which is greater than the particulate material depth 810. Additionally, the particulate material depth throughout the crotch region 807 can be seen generally increasing. In some embodiments, the increase may be generally linear. However, this is not necessarily the case in all embodiments. These differences in the particulate material depths in the rear core region 806, the crotch region 807, and the front core region 808 may result in the described differences in average basis weights within the different regions described previously.

FIG. 18 depicts one example cross-section shape of exemplary absorbent core 750c. For instance, although shown as a generally linear increase in particulate material depth throughout the crotch region 807, this may not be the case in all embodiments. In other contemplated embodiments, the increase throughout the crotch region 807 may be non-linear. Additionally, although a maximum particulate material depth, e.g. particulate depth 812, is shown at an edge of the absorbent core 750c, in other embodiments the maximum particulate material depth may be located still within the front core region 808, but away from an edge of the front core region 808. In these embodiments, the top carrier sheet 875 may have a wavy cross-sectional shape as the particulate material depth may increase throughout the crotch region 807, may peak within the front core region 808, and also decrease within the front core region 808 moving towards an edge of the front core region.

It should be understood, that the specific masking members and process steps described with respect to FIGS. 15-18 may be used in conjunction with any of the processes described in this disclosure, or in separate, distinct processes not disclosed herein. For instance, masking members 700 may be used in conjunction with process 20, 200, or any other process in order to produce absorbent cores having a gradient of basis weights extending from a rear region of the absorbent core a front region of the absorbent core. In further embodiments, the masking members and process steps may be used to produce absorbent cores with different average basis weights between different regions of the cores, such as within the front ear portions, within the central front core region, within the crotch region, within the central rear core region, and within the rear ear portions, as described with respect to FIG. 17. In this manner, particulate material may be directed toward portions of absorbent cores where the particulate material will be more effective in absorbing bodily fluids thereby decreasing the amount of particulate material located in less desirable areas of the cores.

The pulpless absorbent cores the present disclosure may be used in many different absorbent articles. For example, pulpless absorbent cores the present disclosure may be used in diapers and/or training pants in order to help absorb urine and other liquid discharge from babies and toddlers. The pulpless absorbent cores the present disclosure may additionally, or alternatively, be used in incontinence products, disposable underwear, and/or medical garments to help absorb liquid discharge from people who may not be able to control their ability to urinate or defecate. Even further, the pulpless absorbent cores the present disclosure may additionally, or alternatively, be used in feminine care articles to help absorb vaginal discharges. These are just some example absorbent articles in which the pulpless absorbent cores the present disclosure may be used. In general, the pulpless absorbent cores the present disclosure may be used in any suitable absorbent article application.

As various changes could be made in the above without departing from the scope of the invention, it is intended that all matter contained in the above description and shown in the accompanying drawings shall be interpreted as illustrative and not in a limiting sense.

We claim:

1. A method of forming a pulpless absorbent core comprising:
    moving a foraminous forming surface in a machine direction, the foraminous forming surface having unmasked portions and masked portions, and wherein the un-masked portions define an absorbent core region of the foraminous forming surface;
    depositing particulate material at a velocity of less than 1200 meters per minute through a particulate material inlet and at the foraminous forming surface in the absorbent core region while applying a vacuum to the foraminous forming surface;
    depositing a second amount particulate material at a velocity of less than 1200 meters per minute through a second particulate material inlet and at the foraminous forming surface in the absorbent core region while applying a vacuum to the foraminous forming surface;
    and prior to depositing the second amount particulate material, applying adhesive to the deposited first amount of particulate material;
    wherein the absorbent core region comprises:
    a front core region spanning a front third of the absorbent core region;
    a rear core region spanning a rear third of the absorbent core region; and
    a crotch region disposed between the front core region and the rear core region and spanning a middle third of the absorbent core region, the crotch region having a cross-machine direction width that is less than a width of the front core region and less than a width of the rear core region;
    wherein the front core region trails the rear core region in the machine direction; and
    wherein the masked portions of the foraminous forming surface block airflow through the foraminous forming surface to cause greater than 40% of the particulate material deposited in the absorbent core region to locate in the front core region.

2. The method of claim 1, wherein the masked portions of the forming surface comprise masked portions proximate the crotch region, wherein the front core region has a greatest cross-machine direction width, and wherein the masked portions proximate the crotch region extend inward from an edge of the absorbent core region between 10% and 40% of the greatest cross-machine direction width.

3. The method of claim 1, wherein the masked portions of the forming surface comprise masked portions proximate the crotch region, and wherein the masked portions proximate the crotch region comprise an area that is between 25% and 50% of an area defined by a greatest cross-machine direction width of the absorbent core region and a machine direction length of the absorbent core region.

4. The method of claim 1, wherein the front core region has an average basis weight that is between 110% and 170% of an average basis weight of the rear core region.

5. A method of forming an absorbent core comprising:
    advancing a base carrier sheet in a machine direction on a foraminous forming surface, the foraminous forming surface having un-masked portions and masked portions, and wherein the un-masked portions of the foraminous forming surface define an absorbent core region;
    applying a first adhesive onto a top surface of the base carrier sheet;
    advancing the base carrier sheet within a first particulate material delivery chamber;
    depositing a first amount of particulate material at a velocity of less than 1200 meters per minute through a first particulate material inlet disposed within the first particulate material delivery chamber and at the foraminous forming surface in the absorbent core region while applying a vacuum to the foraminous forming surface;
    applying a second adhesive onto the first amount of particulate material outside of the first particulate material delivery chamber;
    advancing the base carrier sheet with the first adhesive, the first amount of particulate material, and the second adhesive into a second particulate material delivery chamber;
    depositing a second amount of particulate material at a velocity of less than 1200 meters per minute through a second particulate material inlet disposed within the second particulate material delivery chamber and at the foraminous forming surface in the absorbent core region while applying a vacuum to the foraminous forming surface; and
    applying a top carrier sheet over the second amount of particulate material,
    wherein the absorbent core region comprises:
    a front core region spanning a first half of the absorbent core region; and
    a rear core region spanning a second half of the absorbent core region;
    wherein the front core region trails the rear core region in the machine direction; and
    wherein the masked portions of the foraminous forming surface block airflow through the foraminous forming surface to cause greater than 60% of the particulate material deposited in the absorbent core region of the foraminous forming surface to locate in the front core region.

6. The method of claim 5, wherein the front core region has an average basis weight between 200 gsm and 800 gsm, and wherein the rear core region has an average basis weight between 100 gsm and 600 gsm.

7. The method of claim 5, wherein the front core region may have an average basis weight that is between 110% and 170% of an average basis weight of the rear core region.

8. The method of claim 5, wherein the first adhesive comprises a hot-melt adhesive, and wherein the second adhesive comprises a spray application aqueous binder (SAAB) adhesive.

9. The method of claim 5, further comprising mixing cellulose fibers with at least one of the first amount of particulate material and the second amount of particulate material before depositing the mixture of the cellulose fibers and the first amount of particulate material and/or the second amount of particulate material at the foraminous forming surface.

* * * * *